(12) United States Patent
Froehler et al.

(10) Patent No.: US 6,235,887 B1
(45) Date of Patent: May 22, 2001

(54) ENHANCED TRIPLE-HELIX AND DOUBLE-HELIX FORMATION DIRECTED BY OLIGONUCLEOTIDES CONTAINING MODIFIED PYRIMIDINES

(75) Inventors: Brian Froehler, Belmont; Robert J. Jones, Millbrae, both of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/338,352

(22) Filed: Nov. 14, 1994

Related U.S. Application Data

(63) Continuation of application No. 07/935,444, filed on Aug. 25, 1992, now abandoned, which is a continuation-in-part of application No. 07/799,824, filed on Nov. 26, 1991, now Pat. No. 5,484,908.

(51) Int. Cl.$^7$ .......................... C07H 21/02; A01N 43/04
(52) U.S. Cl. ...................... 536/23.1; 536/22.1; 514/43; 514/44
(58) Field of Search .................... 536/23.1, 24.3, 536/26.1, 18.7, 22.1, 24.33, 26.8; 514/43, 44

(56) References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |
| 4,725,677 | 2/1988 | Köster et al. | 536/27 |
| 4,959,463 | 9/1990 | Froehler et al. | 536/27 |

FOREIGN PATENT DOCUMENTS

| | | | |
|---|---|---|---|
| 375408 | 6/1990 | (EP) . | |
| 0486477 | 5/1992 | (EP) . | |
| 0492570 | 7/1992 | (EP) . | |
| 0486477 | 5/1993 | (EP) . | |
| WO 88/08001 | 10/1988 | (WO) . | |
| WO 90/06934 | 6/1990 | (WO) . | |
| WO 91/15884 | 12/1990 | (WO) | C12Q/1/68 |
| WO 92/02258 | 2/1992 | (WO) . | |
| WO 92/05186 | 4/1992 | (WO) . | |
| WO 92/06102 | 4/1992 | (WO) . | |
| WO 92/09705 | 6/1992 | (WO) . | |
| WO 92/10590 | 6/1992 | (WO) . | |

OTHER PUBLICATIONS

Uhlmann et al (Jun. 1990) Chemical Reviews 90(4):pp 543–554.*
Maher et al., *Science* (1989) 245:725–730.
Moser and Dervan, *Science* (1987) 238:645–650.
Cooney et al., *Science* (1988) 241:456–459.
Griffin and Dervan, *Science* (1989) 245:967–971.
Beal and Dervan, *Science* (1990) 251:1360–1363.
Lee et al., *Nucleic Acids Res.* (1984) 12:6603–6614.
Povsic and Dervan, *J. Am. Chem. Soc.* (1989) 111:3059–3061.
Vlassov et al., *Nucleic Acids Res.* (1986) 14:4065–4076.
Knorre et al., *Biochimie* (1985) 67:785–789.
Iverson and Dervan, *J. Am. Chem. Soc.* (1987) 109:1241–1243.
Meyer et al., *J. Am. Chem. Soc.* (1989) 111:8517–8519.
Lee et al., *Biochemistry* (1988) 27:3197–3203.
Horne and Dervan, *J. Am. Chem. Soc.* (1990) 112:2435–2437.
Webb and Matteucci, *J. Am. Chem. Soc.* (1986) 108:2764–2765.
Webb and Matteucci, *Nucleic Acids Res.* (1986) 14:7661–7674.
Matteucci and Webb, *Tetrahedon Letters* (1987) 28:2469–2472.
Praseuth et al., *Proc. Natl. Acad. Sci.* (USA) (1988) 85:1349–1353.
Vlassov et al., *Gene* (1988) pp. 313–322.
Fedorova et al., *FEBS* (1988) 228:273–276.
Capobionco et al., *Nucleic Acids Res.* (1990) 18:2661–2669.
van de Sande et al., *Science* (1988) 241:551–557.
Uhlmann et al., *Chem. Reviews* (1990) 90:543–584.
van der Krol et al., *Biotechniques* (1988) 6:958–976.
Balzarini et al., "Incorporation of 5–substituted pyrimidine nucleoside analogs into DNA of a thymidylate synthetase–deficient murine FM3A carcinoma cell line" *Chem. Abstracts* (1985) 7(1):(abstract No. 16283a).
Ötvös et al., "Substrate specificity of DNA polymerases. II. 5–(1–Alkynyl)–dUTPs as substrates of the Klenow DNA polymerase enzyme" *Chem. Abstracts* (1987) 107(23):(abstract No. 214012g).
Felgner et al., "Lipofection: a highly efficient, lipid–mediated DNA–transfection procedure" *Proc. Natl. Acad. Sci. USA* (1987) 84:7413–7417.
Maher et al., "Inhibition of DNA Binding Proteins by Oligonucleotide–Directed Triple Helix Formation" *Science* (1989) 245:725–730.
Moser and Dervan, "Sequence–Specific Cleavage of Double Helical DNA by Triple Helix Formation" *Science* (1987) 238:645–650.

(List continued on next page.)

*Primary Examiner*—Elizabeth F. McElwain
(74) *Attorney, Agent, or Firm*—Woodcock Washburn Kurtz Mackiewicz & Norris LLP

(57) ABSTRACT

Novel oligomers are disclosed which have enhanced ability with respect to forming duplexes or triplexes compared with oligomers containing only conventional bases. The oligomers contain the base analog 5-propynyluracil, 5-propynylcytosine or related analogs. The oligomers of the invention are capable of (i) forming triplexes with various target sequences such as virus or oncogene sequences by coupling into the major groove of a target DNA duplex at physiological pH or (ii) forming duplexes by binding to single-stranded DNA or to RNA encoded by target genes. The oligomers of the invention may be constructed to have any desired sequence, provided the sequence normally includes one or more bases that is replaced with the analogs of the invention. Compositions of the invention can be used for diagnostic purposes in order to detect viruses or disease conditions.

7 Claims, No Drawings

OTHER PUBLICATIONS

Cooney et al., "Site–Specific Oligonucleotide Binding Represses Transcription of the Human c–myc Gene In Vitro" *Science* (1988) 241:456–459.

Griffin and Dervan, "Recognition of Thymine–Adenine Base Pairs by Guanine in a Pyrimidine Triple Helix Motif" *Science* (1989) 245:967–971.

Beal and Dervan, "Second Structural Motif for Recognition of DNA by Oligonucleotide–Directed Triple–Helix Formation" *Science* (1990) 251:1360–1363.

Lee et al., "Poly(pyrimidine)–poly(purine) synthetic DNAs containing 5–methylcytosine form stable triplexes at neutral pH" *Nucleic Acids Res.* (1984) 12:6603–6614.

Povsic and Dervan, "Triple Helix Formation by Oligonucleotides on DNA Extended to the Physiological pH Range" *J. Am. Chem. Soc.* (1989) 111:3059–3061.

Vlassov et al., "Complementary addressed modification and cleavage of a single stranded DNA fragment with alkylating oligonucleotide derivatives" *Nucleic Acids Res.* (1986) 14:4065–4076.

Knorre et al., "Reactive oligonucleotide derivatives and sequence-specific modification of nucleic acids" Biochimie (1985) 67:785–789.

Iverson and Dervan, "Nonenzymatic Sequence–Specific Cleavage of Single–Stranded DNA to Nucleotide Resolution DNA Methyl Thioether Probes" *J. Am. Chem. Soc.* (1987) 109:1241–1243.

Meyer et al., "Efficient, specific crosslinking and cleavage of DNA by stable, synthetic complementary oligonucleotides" *J. Am. Chem. Soc.* (1989) 111:8517–8519.

Lee et al., "Interaction of psorlen–derivatized oligodeoxyribonucleoside methylphosphonates with single stranded DNA" *Biochemistry* (1988) 27:3197–3203.

Horne et al., "Recognition of mixed–sequence duplex DNA by alternate–strand triple helix formation" *J. Am. Chem. Soc.* (1990) 112:2435–2437.

Webb et al., "Sequence–specific cross–linking of deoxyoligonucleotides via hybridization–triggered alkylation" *J. Am. Chem. Soc.* (1986) 108:2764–2765.

Webb et al., "Hybridization triggered cross–linking of deoxyoligonucleotides" *Nucleic Acids Res.* (1986) 14:7661–7674.

Matteucci et al., "Synthesis and crosslinking properties of a deoxyoligonucleotide containing $N^6$, $N^6$–ethanodeoxyadenosine" *Tetrahedron Letters* (1987) 28:2469–2472.

Praseuth et al., "Sequence–specific binding and photocrosslinking of α and β oligonucleotides to the major groove of DNA via triple–helix formation" *Proc. Natl. Acad. Sci. (USA)* (1988) 85:1349–1353.

Vlassov et al., "Modified oligodeoxyribonucleotides" *Gene* (1988) pp. 313–322.

Fedorova et al., "Complementary addressed modification of double–stranded DNA within a ternary complex" *FEBS* (1988) 228:273–276.

Capobionco et al., "One pot solution synthesis of cyclic oligodeoxyribnucleotides" *Nucleic Acids Res.* (1990) 18:2661–2669.

van de Sande et al., "Parallel stranded DNA" *Science* (1988) 241:551–557.

Uhlmann et al., "Antisense oligonucleotides: a new therapeutic principle" *Chem. Reviews* (1990) 90:543–584.

van der Krol et al., "Modulation of eukaryotic gene expression by complementary RNA or DNA sequences" *Biotechniques* (1988) 6:958–976.

Augustyns et al., "Incorporation of hexose nucleoside analogues into oligonucleotides: synthesis, base–pairing properties and enzymatic stability" *Nucl. Acids Res.* (1992) 20(18):4711–4716.

Chiang et al., "Antisense oligonucleotides inhibit intercellular adhesion molecule 1 expression by two distinct mechanisms" *J. Biol. Chem.* (1991) 266(27):18162–18171.

Clivio et al., "Synthesis of dinucleotide phosphates containing sulfur substituted nucleobases: 4–thiouracil, 4–thiothymine and 6–mercaptopurine" *Tetrahedron Letters* (1992) 33(1):69–72.

Connolly et al., "Synthesis and properties of oligonucleotides containing 4–thiothymidine, 5–methyl–2–pyrimidinone–1–β–D(2'–deoxyriboside) and 2–thiothymidine" *Nucl. Acids Res.* (1989) 17(13):4957–4974.

DeClercq et al., "Nucleic acid related compounds. 40. Synthesis and biological activities of 5–Alkynyluracil nucleosides" *J. Med. Chem.* (1983) 26:661–666.

Egholm et al., "Peptide nucleic acids (PNA): oligonucleotide analogues with an achiral peptide backbone" *J. Amer. Chem. Soc.* (1992) 114:1895–1897.

Froehler et al., "Triple–helix formation by oligonucleotides containing the carbocyclic analogs of thymidine and 5–methyl–2'–deoxycytidine" *J. Amer. Chem. Soc.* (1992) 114:8820–8822.

Froehler et al., "Oligodeoxynucleotides containing C–5 propyne analogs of 2'–deoxyuridine and 2'–deoxycytidine" *Tetrahedron Letters* (1992) 33(37):5307–5310.

Froehler et al., "Triple–helix formation and cooperative binding by oligonucleotides with a 3'–3' internucleotide junction" *Biochemistry* (1992) 31:1603–1609.

Goodchild et al., "Structural requirements of olefinic 5–substituted deoxyuridines for antiherpes activities" *J. Med. Chem.* (1983) 26:1252–1257.

Krawczyk et al., "Oligonucleotide–mediated triple helix formation using an $N^3$–protonated deoxycytidine analog exhibiting pH–independent binding within the physiological range" *Proc. Natl. Acad. Sci. USA* (1992) 89:3761–3764.

Ono et al., "Triplex formation of an oligonucleotide containing 2'–O–methylpseudoisocytidine with a DNA duplex at neutral pH" *J. Org. Chem.* (1992) 57:3225–3230.

Ötvös et al., "Substrate specificity of DNA polymerases. I. Enzyme–catalyzed incorporation of 5–(1–alkenyl)–2'–deoxyuridines into DNA" *Nucl. Acids Res.* (1987) 15(4):1763–1777.

Rahim et al., "5–alkynyl pyrimidine nucleosides as potent selective inhibitors of varicella–zoster virus" *Antiviral Chem. & Chemother.* (1992) 3(5):293–297.

Reynolds et al., "Synthesis of thymidine dimers containing internucleoside sulfonate and sulfonamide linkages" *J. Org. Chem.* (1992) 57:2983–2985.

Robins et al., "Nucleic acid related compounds. 38. Smooth and high–yield iodination and chlorination at C–5 of uracil bases and p–toluyl–protected nucleosides" *Can. J. Chem.* (1982) 60:554–557.

Shaw et al., "Specific, high–efficiency, triple–helix–mediated cross–linking to duplex DNA" *J. Amer. Chem. Soc.* (1991) 113:7765–7766.

Valkó et al., "Correlation of nucleotide incorporation rate and HPLC retention parameters of substituted nucleosides" *J. Liquid Chromatog.* (1989) 12(11):2103–2116.

Valkó et al., "Application of chromatographic retention data in an investigation of a quantitative structure–nucleotide incorporation rate relationship" *J. Chromatog.* (1990) 506:35–44.

Vasseur et al., "Oligonucleosides: synthesis of a novel methylhydroxylamine–linked nucleoside dimer and its incorporation into antisense sequences" *J. Amer. Chem. Soc.* (1992) 114:4006–4007.

Wigernick et al., "5–(5–Bromothein–2–yl)–2'–deoxyuridine and 5–(5–chlorothein–2–yl)–2'–deoxyuridine are equipotent to (E)–5–(2–bromovinyl)–2'–deoxyuridine in the inhibition of herpes simplex virus type 1 replication" *J. Med. Chem.* (1991) 34:2383–2389.

Young et al., "Triple helix formation inhibits transcription elongation in vitro" *Proc. Natl. Acad. Sci. USA* (1991) 88:10023–10026.

Albretsen et al, "Optimal Conditions for Hybridization with Oligonucleotides: A Study with myc–Oncogene DNA Probes," Anal Biochem 170:193–202 (1988).

Casey et al, "Rates of formation and thermal stabilities of RNA:DNA and DNA:DNA duplexes at high concentration of formamide," Nuc Acids Res 4(5):1539–1552 (1977).

Hamaguchi et al, "The Effect of Electrolytes on the Stability of the Deoxyribonucleate Helix," J Am Chem Soc 84:1329–1338 (1962).

Hutton, James R., "Renaturation kinetics and thermal stability of DNA in aqueous solutions of formamide and urea," Nuc Acids Res 4(10):3537–3555 (Oct. 1977).

Matthews et al, "Analytical Strategies for the Use of DNA Probes," Anal Biochem 169:1–25 (1988).

Murakami et al, "Highly sensitive detection of DNA using enzyme–linked DNA–probe. 1. Colorimetric and fluorometric detection," Nuc Acids Res 17(14):5587–5595 (1989).

Nielsen et al., "Sequence–Selective Recognition of DNA by Strand Displacement with a Thymine–Substituted Polyamide," Science 254:1497–1500 (1991).

Quartin et al, "Effect of Ionic Strength on the Hybridization of Oligodeoxynucleotides with Reduced Charge Due to Methylphosphonate Linkages to Unmodified Oligodeoxynucleotides Containing the Complementary Sequence," Biochem 28:1040–1047 (1989).

Thompson et al, "Molecular Hybridization with RNA Probes in Concentrated Solutions of Guanidine Thiocyanate," Anal Biochem 163:281–291 (1987).

Van Ness et al, "The use of oligodeoxynucleotide probes in chaotrope–based hybridization solutions," Nuc Acids Res 19(19):5143–5151 (1991).

* cited by examiner

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 4 base pairs
      (B) TYPE: nucleic acid
      (C) STRANDEDNESS: single
      (D) TOPOLOGY: linear (xi) SEQUENCE DESCRIPTION: SEQ ID NO:1:

ATAT          4

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 2
      (D) OTHER INFORMATION: /note= "This position is C' = 5 methyl cytosine."

(ix) FEATURE:
      (A) NAME/KEY: modified_base

```
        (B) LOCATION: 4
        (D) OTHER INFORMATION: /note= "This position is C' = 5
            methyl cytosine."

(ix) FEATURE:
        (A) NAME/KEY: modified_base
        (B) LOCATION: 6
        (D) OTHER INFORMATION: /note= "This position is C' = 5
            methyl cytosine."

(ix) FEATURE:
        (A) NAME/KEY: modified_base
        (B) LOCATION: 8
        (D) OTHER INFORMATION: /note= "This position is C' = 5
            methyl cytosine."

(ix) FEATURE:
        (A) NAME/KEY: modified_base
        (B) LOCATION: 10
        (D) OTHER INFORMATION: /note= "This position is C' = 5
            methyl cytosine."

(xi) SEQUENCE DESCRIPTION: SEQ ID NO:2:

TNTNTNTNTN TTTTT                                                    15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 2
        (D) OTHER INFORMATION: /note= "This position is C' = 5
            methyl cytosine."

(ix) FEATURE:
        (A) NAME/KEY: modified_base
        (B) LOCATION: 4
        (D) OTHER INFORMATION: /note= "This position is C' = 5
            methyl cytosine."

(ix) FEATURE:
        (A) NAME/KEY: modified_base
        (B) LOCATION: 6
        (D) OTHER INFORMATION: /note= "This position is C' = 5
            methyl cytosine."

(ix) FEATURE:
        (A) NAME/KEY: modified_base
        (B) LOCATION: 8
        (D) OTHER INFORMATION: /note= "This position is C' = 5
            methyl cytosine."

(ix) FEATURE:
        (A) NAME/KEY: modified_base
        (B) LOCATION: 10
        (D) OTHER INFORMATION: /note= "This position is C' = 5
            methyl cytosine."

(ix) FEATURE:
        (A) NAME/KEY: modified_base
        (B) LOCATION: 11
        (D) OTHER INFORMATION: /note= "This position is U* =
            5-propynyl uracil."

(ix) FEATURE:
        (A) NAME/KEY: modified_base
        (B) LOCATION: 12
        (D) OTHER INFORMATION: /note= "This position is U* =
            5-propynyl uracil."

(ix) FEATURE:
        (A) NAME/KEY: modified_base
```

(B) LOCATION: 13
                (D) OTHER INFORMATION: /note= "This position is U* =
                    5-propynyl uracil."

(ix) FEATURE:
                (A) NAME/KEY: modified_base
                (B) LOCATION: 14
                (D) OTHER INFORMATION: /note= "This position is U* =
                    5-propynyl uracil."

(ix) FEATURE:
                (A) NAME/KEY: modified_base
                (B) LOCATION: 15
                (D) OTHER INFORMATION: /note= "This position is U* =
                    5-propynyl uracil."

(xi) SEQUENCE DESCRIPTION: SEQ ID NO:3:

TNTNTNTNTN NNNNN                                                              15

(2) INFORMATION FOR SEQ ID NO:4:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ix) FEATURE:
                (A) NAME/KEY: modified_base
                (B) LOCATION: 2
                (D) OTHER INFORMATION: /note= "This position is C' = 5
                    methyl cytosine."

(ix) FEATURE:
                (A) NAME/KEY: modified_base
                (B) LOCATION: 4
                (D) OTHER INFORMATION: /note= "This position is C' = 5
                    methyl cytosine."

(ix) FEATURE:
                (A) NAME/KEY: modified_base
                (B) LOCATION: 6
                (D) OTHER INFORMATION: /note= "This position is C' = 5
                    methyl cytosine."

(ix) FEATURE:
                (A) NAME/KEY: modified_base
                (B) LOCATION: 7
                (D) OTHER INFORMATION: /note= "This position is U* =
                    5-propynyl uracil."

(ix) FEATURE:
                (A) NAME/KEY: modified_base
                (B) LOCATION: 8
                (D) OTHER INFORMATION: /note= "This position is C' = 5
                    methyl cytosine."

(ix) FEATURE:
                (A) NAME/KEY: modified_base
                (B) LOCATION: 9
                (D) OTHER INFORMATION: /note= "This position is U* =
                    5-propynyl uracil."

(ix) FEATURE:
                (A) NAME/KEY: modified_base
                (B) LOCATION: 10
                (D) OTHER INFORMATION: /note= "This position is C' = 5
                    methyl cytosine."

(ix) FEATURE:
                (A) NAME/KEY: modified_base
                (B) LOCATION: 11
                (D) OTHER INFORMATION: /note= "This position is U* =
                    5-propynyl uracil."

(ix) FEATURE:
                (A) NAME/KEY: modified_base (B) LOCATION: 13
        (D) OTHER INFORMATION: /note= "This position is U* =
            5-propynyl uracil."

(ix) FEATURE:
        (A) NAME/KEY: modified_base
        (B) LOCATION: 15
        (D) OTHER INFORMATION: /note= "This position is U* =
            5-propynyl uracil."

(xi) SEQUENCE DESCRIPTION: SEQ ID NO:4:

TNTNTNNNNN NTNTN                                                    15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:5:

AGAGAGAGAG AAAAA                                                    15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 2
        (D) OTHER INFORMATION: /note= "This position is C* =
            5-propynyl cytosine."

(ix) FEATURE:
        (A) NAME/KEY: modified_base
        (B) LOCATION: 4
        (D) OTHER INFORMATION: /note= "This position is C* =
            5-propynyl cytosine."

(ix) FEATURE:
        (A) NAME/KEY: modified_base
        (B) LOCATION: 6
        (D) OTHER INFORMATION: /note= "This position is C* =
            5-propynyl cytosine."

(ix) FEATURE:
        (A) NAME/KEY: modified_base
        (B) LOCATION: 8
        (D) OTHER INFORMATION: /note= "This position is C* =
            5-propynyl cytosine."

(ix) FEATURE:
        (A) NAME/KEY: modified_base
        (B) LOCATION: 10
        (D) OTHER INFORMATION: /note= "This position is C* =
            5-propynyl cytosine."

(xi) SEQUENCE DESCRIPTION: SEQ ID NO:6:

TNTNTNTNTN TTTTT                                                    15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:7:

AAAAAGAGAG AGAGA                                           15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1
        (D) OTHER INFORMATION: /note= "This position is U* =
            5-propynyl uracil."

(ix) FEATURE:
        (A) NAME/KEY: modified_base
        (B) LOCATION: 2
        (D) OTHER INFORMATION: /note= "This position is C' = 5
            methyl cytosine."

(ix) FEATURE:
        (A) NAME/KEY: modified_base
        (B) LOCATION: 3
        (D) OTHER INFORMATION: /note= "This position is U* =
            5-propynyl uracil."

(ix) FEATURE:
        (A) NAME/KEY: modified_base
        (B) LOCATION: 4
        (D) OTHER INFORMATION: /note= "This position is C' = 5
            methyl cytosine."

(ix) FEATURE:
        (A) NAME/KEY: modified_base
        (B) LOCATION: 5
        (D) OTHER INFORMATION: /note= "This position is U* =
            5-propynyl uracil."

(ix) FEATURE:
        (A) NAME/KEY: modified_base
        (B) LOCATION: 6
        (D) OTHER INFORMATION: /note= "This position is C' = 5
            methyl cytosine."

(ix) FEATURE:
        (A) NAME/KEY: modified_base
        (B) LOCATION: 7
        (D) OTHER INFORMATION: /note= "This position is U* =
            5-propynyl uracil."

(ix) FEATURE:
        (A) NAME/KEY: modified_base
        (B) LOCATION: 8
        (D) OTHER INFORMATION: /note= "This position is C' = 5
            methyl cytosine."

(ix) FEATURE:
        (A) NAME/KEY: modified_base
        (B) LOCATION: 9
        (D) OTHER INFORMATION: /note= "This position is U* =
            5-propynyl uracil."

(ix) FEATURE:
        (A) NAME/KEY: modified_base
        (B) LOCATION: 10
        (D) OTHER INFORMATION: /note= "This position is C' = 5
            methyl cytosine."

(ix) FEATURE:
        (A) NAME/KEY: modified_base
        (B) LOCATION: 11
        (D) OTHER INFORMATION: /note= "This position is U* =
            5-propynyl uracil."

(ix) FEATURE:
                 (A) NAME/KEY: modified_base
                 (B) LOCATION: 12
                 (D) OTHER INFORMATION: /note= "This position is U* =
                     5-propynyl uracil."

(ix) FEATURE:
                 (A) NAME/KEY: modified_base
                 (B) LOCATION: 13
                 (D) OTHER INFORMATION: /note= "This position is U* =
                     5-propynyl uracil."

(ix) FEATURE:
                 (A) NAME/KEY: modified_base
                 (B) LOCATION: 14
                 (D) OTHER INFORMATION: /note= "This position is U* =
                     5-propynyl uracil."

(ix) FEATURE:
                 (A) NAME/KEY: modified_base
                 (B) LOCATION: 15
                 (D) OTHER INFORMATION: /note= "This position is U* =
                     5-propynyl uracil."

(xi) SEQUENCE DESCRIPTION: SEQ ID NO:8:

NNNNNNNNNN NNNNN                                                          15

(2) INFORMATION FOR SEQ ID NO:9:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ix) FEATURE:
         (A) NAME/KEY: modified_base
         (B) LOCATION: 2
         (D) OTHER INFORMATION: /note= "This position is C' = 5
             methyl cytosine."

(ix) FEATURE:
         (A) NAME/KEY: modified_base
         (B) LOCATION: 4
         (D) OTHER INFORMATION: /note= "This position is C' = 5
             methyl cytosine."

(ix) FEATURE:
         (A) NAME/KEY: modified_base
         (B) LOCATION: 6
         (D) OTHER INFORMATION: /note= "This position is C' = 5
             methyl cytosine."

(ix) FEATURE:
         (A) NAME/KEY: modified_base
         (B) LOCATION: 7
         (D) OTHER INFORMATION: /note= "This position is U'= bdU."

(ix) FEATURE:
         (A) NAME/KEY: modified_base
         (B) LOCATION: 8
         (D) OTHER INFORMATION: /note= "This position is C' = 5
             methyl cytosine."

(ix) FEATURE:
         (A) NAME/KEY: modified_base
         (B) LOCATION: 9
         (D) OTHER INFORMATION: /note= "This position is U' = bdU."

(ix) FEATURE:
         (A) NAME/KEY: modified_base
         (B) LOCATION: 11
         (D) OTHER INFORMATION: /note= "This position is U' = bdU."

(ix) FEATURE:
         (A) NAME/KEY: modified_base
         (B) LOCATION: 13

(D) OTHER INFORMATION: /note= "This position is U' = bdU."

(ix) FEATURE:
            (A) NAME/KEY: modified_base
            (B) LOCATION: 15
            (D) OTHER INFORMATION: /note= "This position is U' = bdU."

(xi) SEQUENCE DESCRIPTION: SEQ ID NO:9:

TNTNTNNNNC NTNTN                                                                15

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 2
            (D) OTHER INFORMATION: /note= "This position is C' = 5
                methyl cytosine."

(ix) FEATURE:
            (A) NAME/KEY: modified_base
            (B) LOCATION: 4
            (D) OTHER INFORMATION: /note= "This position is C' = 5
                methyl cytosine."

(ix) FEATURE:
            (A) NAME/KEY: modified_base
            (B) LOCATION: 6
            (D) OTHER INFORMATION: /note= "This position is C' = 5
                methyl cytosine."

(ix) FEATURE:
            (A) NAME/KEY: modified_base
            (B) LOCATION: 8
            (D) OTHER INFORMATION: /note= "This position is C' = 5
                methyl cytosine."

(ix) FEATURE:
            (A) NAME/KEY: modified_base
            (B) LOCATION: 10
            (D) OTHER INFORMATION: /note= "This position is C' = 5
                methyl cytosine."

(ix) FEATURE:
            (A) NAME/KEY: modified_base
            (B) LOCATION: 11
            (D) OTHER INFORMATION: /note= "This position is U' = bdU."

(ix) FEATURE:
            (A) NAME/KEY: modified_base
            (B) LOCATION: 12
            (D) OTHER INFORMATION: /note= "This position is U' = bdU."

(ix) FEATURE:
            (A) NAME/KEY: modified_base
            (B) LOCATION: 13
            (D) OTHER INFORMATION: /note= "This position is U' = bdU."

(ix) FEATURE:
            (A) NAME/KEY: modified_base
            (B) LOCATION: 14
            (D) OTHER INFORMATION: /note= "This position is U' = bdU."

(ix) FEATURE:
            (A) NAME/KEY: modified_base
            (B) LOCATION: 15
            (D) OTHER INFORMATION: /note= "This position is U' = bdU."

(xi) SEQUENCE DESCRIPTION: SEQ ID NO:10:

TNTNTNTNTN NNNNN                                                                15

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

AGAGAGAGAG AAAAAGGA                                                         18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

TCTCTCTCTC TTTTTCCT                                                         18

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:13:

AAAAAGAGAG AGAGA                                                            15

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1
        (D) OTHER INFORMATION: /note= "This position is U* =
            5-propynyl uracil."

(ix) FEATURE:
        (A) NAME/KEY: modified_base
        (B) LOCATION: 2
        (D) OTHER INFORMATION: /note= "This position is C* =
            5-propynyl cytosine."

(ix) FEATURE:
        (A) NAME/KEY: modified_base
        (B) LOCATION: 3
        (D) OTHER INFORMATION: /note= "This position is U* =
            5-propynyl uracil."

(ix) FEATURE:
        (A) NAME/KEY: modified_base
        (B) LOCATION: 4
        (D) OTHER INFORMATION: /note= "This position is C* =
            5-propynyl cytosine."

(ix) FEATURE:
        (A) NAME/KEY: modified_base
        (B) LOCATION: 6
        (D) OTHER INFORMATION: /note= "This position is C* =
            5-propynyl cytosine."

(ix) FEATURE:

(A) NAME/KEY: modified_base
            (B) LOCATION: 7
            (D) OTHER INFORMATION: /note= "This position is U* =
                5-propynyl uracil."

(ix) FEATURE:
            (A) NAME/KEY: modified_base
            (B) LOCATION: 8
            (D) OTHER INFORMATION: /note= "This position is C* =
                5-propynyl cytosine."

(ix) FEATURE:
            (A) NAME/KEY: modified_base
            (B) LOCATION: 9
            (D) OTHER INFORMATION: /note= "This position is U* =
                5-propynyl uracil."

(ix) FEATURE:
            (A) NAME/KEY: modified_base
            (B) LOCATION: 10
            (D) OTHER INFORMATION: /note= "This position is U* =
                5-propynyl uracil."

(ix) FEATURE:
            (A) NAME/KEY: modified_base
            (B) LOCATION: 11
            (D) OTHER INFORMATION: /note= "This position is C* =
                5-propynyl cytosine."

(ix) FEATURE:
            (A) NAME/KEY: modified_base
            (B) LOCATION: 12
            (D) OTHER INFORMATION: /note= "This position is U* =
                5-propynyl uracil."

(ix) FEATURE:
            (A) NAME/KEY: modified_base
            (B) LOCATION: 13
            (D) OTHER INFORMATION: /note= "This position is U* =
                5-propynyl uracil."

(ix) FEATURE:
            (A) NAME/KEY: modified_base
            (B) LOCATION: 14
            (D) OTHER INFORMATION: /note= "This position is U* =
                5-propynyl uracil."

(xi) SEQUENCE DESCRIPTION: SEQ ID NO:14:

NCNCNCNCNN NNNNN                                                                15

(2) INFORMATION FOR SEQ ID NO:15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 6
            (D) OTHER INFORMATION: /note= "This position is C' = 5
                methyl cytosine."

(ix) FEATURE:
            (A) NAME/KEY: modified_base
            (B) LOCATION: 9
            (D) OTHER INFORMATION: /note= "This position is C' = 5
                methyl cytosine."

(ix) FEATURE:
            (A) NAME/KEY: modified_base
            (B) LOCATION: 17
            (D) OTHER INFORMATION: /note= "This position is C' = 5
                methyl cytosine."

(ix) FEATURE:

(A) NAME/KEY: modified_base
            (B) LOCATION: 20
            (D) OTHER INFORMATION: /note= "This position is C' = 5
                methyl cytosine."

(xi) SEQUENCE DESCRIPTION: SEQ ID NO:15:

ATTTTNTTNA TTTTTTNTTN                                                        20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 2
        (D) OTHER INFORMATION: /note= "This position is U* =
            5-propynyl uracil."

(ix) FEATURE:
        (A) NAME/KEY: modified_base
        (B) LOCATION: 3
        (D) OTHER INFORMATION: /note= "This position is U* =
            5-propynyl uracil."

(ix) FEATURE:
        (A) NAME/KEY: modified_base
        (B) LOCATION: 4
        (D) OTHER INFORMATION: /note= "This position is U* =
            5-propynyl uracil."

(ix) FEATURE:
        (A) NAME/KEY: modified_base
        (B) LOCATION: 5
        (D) OTHER INFORMATION: /note= "This position is U* =
            5-propynyl uracil."

(ix) FEATURE:
        (A) NAME/KEY: modified_base
        (B) LOCATION: 6
        (D) OTHER INFORMATION: /note= "This position is C' = 5
            methyl cytosine."

(ix) FEATURE:
        (A) NAME/KEY: modified_base
        (B) LOCATION: 7
        (D) OTHER INFORMATION: /note= "This position is U* =
            5-propynyl uracil."

(ix) FEATURE:
        (A) NAME/KEY: modified_base
        (B) LOCATION: 8
        (D) OTHER INFORMATION: /note= "This position is U* =
            5-propynyl uracil."

(ix) FEATURE:
        (A) NAME/KEY: modified_base
        (B) LOCATION: 9
        (D) OTHER INFORMATION: /note= "This position is C' = 5
            methyl cytosine."

(ix) FEATURE:
        (A) NAME/KEY: modified_base
        (B) LOCATION: 11
        (D) OTHER INFORMATION: /note= "This position is U* =
            5-propynyl uracil."

(ix) FEATURE:
        (A) NAME/KEY: modified_base
        (B) LOCATION: 12
        (D) OTHER INFORMATION: /note= "This position is U* =
            5-propynyl uracil."

(ix) FEATURE:

(A) NAME/KEY: modified_base
                (B) LOCATION: 13
                (D) OTHER INFORMATION: /note= "This position is U* =
                    5-propynyl uracil."

(ix) FEATURE:
                (A) NAME/KEY: modified_base
                (B) LOCATION: 14
                (D) OTHER INFORMATION: /note= "This position is U* =
                    5-propynyl uracil."

(ix) FEATURE:
                (A) NAME/KEY: modified_base
                (B) LOCATION: 15
                (D) OTHER INFORMATION: /note= "This position is U* =
                    5-propynyl uracil."

(ix) FEATURE:
                (A) NAME/KEY: modified_base
                (B) LOCATION: 16
                (D) OTHER INFORMATION: /note= "This position is U* =
                    5-propynyl uracil."

(ix) FEATURE:
                (A) NAME/KEY: modified_base
                (B) LOCATION: 17
                (D) OTHER INFORMATION: /note= "This position is C' = 5
                    methyl cytosine."

(ix) FEATURE:
                (A) NAME/KEY: modified_base
                (B) LOCATION: 18
                (D) OTHER INFORMATION: /note= "This position is U* =
                    5-propynyl uracil."

(ix) FEATURE:
                (A) NAME/KEY: modified_base
                (B) LOCATION: 19
                (D) OTHER INFORMATION: /note= "This position is U* =
                    5-propynyl uracil."

(ix) FEATURE:
                (A) NAME/KEY: modified_base
                (B) LOCATION: 20
                (D) OTHER INFORMATION: /note= "This position is C' = 5
                    methyl cytosine."

(xi) SEQUENCE DESCRIPTION: SEQ ID NO:16:

ANNNNNNNNA NNNNNNNNNN                                                    20

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
                (A) NAME/KEY: modified_base
                (B) LOCATION: 2
                (D) OTHER INFORMATION: /note= "This position is U* =
                    5-propynyl uracil."

(ix) FEATURE:
                (A) NAME/KEY: modified_base
                (B) LOCATION: 3
                (D) OTHER INFORMATION: /note= "This position is U* =
                    5-propynyl uracil."

(ix) FEATURE:
                (A) NAME/KEY: modified_base
                (B) LOCATION: 4
                (D) OTHER INFORMATION: /note= "This position is U* =
                    5-propynyl uracil."

(ix) FEATURE:

```
        (A) NAME/KEY: modified_base
        (B) LOCATION: 5
        (D) OTHER INFORMATION: /note= "This position is U* =
            5-propynyl uracil."

(ix) FEATURE:
        (A) NAME/KEY: modified_base
        (B) LOCATION: 6
        (D) OTHER INFORMATION: /note= "This position is C* = 5
            propynyl cytosine."

(ix) FEATURE:
        (A) NAME/KEY: modified_base
        (B) LOCATION: 7
        (D) OTHER INFORMATION: /note= "This position is U* =
            5-propynyl uracil."

(ix) FEATURE:
        (A) NAME/KEY: modified_base
        (B) LOCATION: 8
        (D) OTHER INFORMATION: /note= "This position is U* =
            5-propynyl uracil."

(ix) FEATURE:
        (A) NAME/KEY: modified_base
        (B) LOCATION: 9
        (D) OTHER INFORMATION: /note= "This position is C* =
            5-propynyl cytosine."

(ix) FEATURE:
        (A) NAME/KEY: modified_base
        (B) LOCATION: 11
        (D) OTHER INFORMATION: /note= "This position is U* =
            5-propynyl uracil."

(ix) FEATURE:
        (A) NAME/KEY: modified_base
        (B) LOCATION: 12
        (D) OTHER INFORMATION: /note= "This position is U* =
            5-propynyl uracil."

(ix) FEATURE:
        (A) NAME/KEY: modified_base
        (B) LOCATION: 13
        (D) OTHER INFORMATION: /note= "This position is U* =
            5-propynyl uracil."

(ix) FEATURE:
        (A) NAME/KEY: modified_base
        (B) LOCATION: 14
        (D) OTHER INFORMATION: /note= "This position is U* =
            5-propynyl uracil."

(ix) FEATURE:
        (A) NAME/KEY: modified_base
        (B) LOCATION: 15
        (D) OTHER INFORMATION: /note= "This position is U* =
            5-propynyl uracil."

(ix) FEATURE:
        (A) NAME/KEY: modified_base
        (B) LOCATION: 16
        (D) OTHER INFORMATION: /note= "This position is U* =
            5-propynyl uracil."

(ix) FEATURE:
        (A) NAME/KEY: modified_base
        (B) LOCATION: 17
        (D) OTHER INFORMATION: /note= "This position is C* =
            5-propynyl cytosine."

(ix) FEATURE:
        (A) NAME/KEY: modified_base
        (B) LOCATION: 18
        (D) OTHER INFORMATION: /note= "This position is U* =
            5-propynyl uracil."

(ix) FEATURE:
        (A) NAME/KEY: modified_base
```

(B) LOCATION: 19
            (D) OTHER INFORMATION: /note= "This position is U* =
                5-propynyl uracil."

(ix) FEATURE:
            (A) NAME/KEY: modified_base
            (B) LOCATION: 20
            (D) OTHER INFORMATION: /note= "This position is C* =
                5-propynyl cytosine."

(xi) SEQUENCE DESCRIPTION: SEQ ID NO:17:

ANNNNNNNNA NNNNNNNNNN                                                      20

(2) INFORMATION FOR SEQ ID NO:18:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 2
            (D) OTHER INFORMATION: /note= "This position is U* =
                5-propynyl uracil."

(ix) FEATURE:
            (A) NAME/KEY: modified_base
            (B) LOCATION: 3
            (D) OTHER INFORMATION: /note= "This position is U* =
                5-propynyl uracil."

(ix) FEATURE:
            (A) NAME/KEY: modified_base
            (B) LOCATION: 4
            (D) OTHER INFORMATION: /note= "This position is U* =
                5-propynyl uracil."

(ix) FEATURE:
            (A) NAME/KEY: modified_base
            (B) LOCATION: 5
            (D) OTHER INFORMATION: /note= "This position is C* =
                5-propynyl cytosine."

(ix) FEATURE:
            (A) NAME/KEY: modified_base
            (B) LOCATION: 6
            (D) OTHER INFORMATION: /note= "This position is U* =
                5-propynyl uracil."

(ix) FEATURE:
            (A) NAME/KEY: modified_base
            (B) LOCATION: 7
            (D) OTHER INFORMATION: /note= "This position is U* =
                5-propynyl uracil."

(ix) FEATURE:
            (A) NAME/KEY: modified_base
            (B) LOCATION: 8
            (D) OTHER INFORMATION: /note= "This position is C* =
                5-propynyl cytosine."

(ix) FEATURE:
            (A) NAME/KEY: modified_base
            (B) LOCATION: 10
            (D) OTHER INFORMATION: /note= "This position is U* =
                5-propynyl uracil."

(ix) FEATURE:
            (A) NAME/KEY: modified_base
            (B) LOCATION: 11
            (D) OTHER INFORMATION: /note= "This position is U* =
                5-propynyl uracil."

(ix) FEATURE:
            (A) NAME/KEY: modified_base

```
        (B) LOCATION: 12
        (D) OTHER INFORMATION: /note= "This position is U* =
            5-propynyl uracil."

(ix) FEATURE:
        (A) NAME/KEY: modified_base
        (B) LOCATION: 13
        (D) OTHER INFORMATION: /note= "This position is U* =
            5-propynyl uracil."

(ix) FEATURE:
        (A) NAME/KEY: modified_base
        (B) LOCATION: 14
        (D) OTHER INFORMATION: /note= "This position is U* =
            5-propynyl uracil."

(ix) FEATURE:
        (A) NAME/KEY: modified_base
        (B) LOCATION: 15
        (D) OTHER INFORMATION: /note= "This position is U* =
            5-propynyl uracil."

(ix) FEATURE:
        (A) NAME/KEY: modified_base
        (B) LOCATION: 16
        (D) OTHER INFORMATION: /note= "This position is C* =
            5-propynyl cytosine."

(ix) FEATURE:
        (A) NAME/KEY: modified_base
        (B) LOCATION: 17
        (D) OTHER INFORMATION: /note= "This position is U* =
            5-propynyl uracil."

(ix) FEATURE:
        (A) NAME/KEY: modified_base
        (B) LOCATION: 18
        (D) OTHER INFORMATION: /note= "This position is U* =
            5-propynyl uracil."

(ix) FEATURE:
        (A) NAME/KEY: modified_base
        (B) LOCATION: 19
        (D) OTHER INFORMATION: /note= "This position is C* =
            5-propynyl cytosine."

(xi) SEQUENCE DESCRIPTION: SEQ ID NO:18:

ANNNNNNNNAN NNNNNNNNN                                                     19

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1
        (D) OTHER INFORMATION: /note= "This position is C* =
            5-propynyl cytosine."

(ix) FEATURE:
        (A) NAME/KEY: modified_base
        (B) LOCATION: 2
        (D) OTHER INFORMATION: /note= "This position is U* =
            5-propynyl uracil."

(ix) FEATURE:
        (A) NAME/KEY: modified_base
        (B) LOCATION: 3
        (D) OTHER INFORMATION: /note= "This position is U* =
            5-propynyl uracil."

(ix) FEATURE:
        (A) NAME/KEY: modified_base
```

(B) LOCATION: 4
            (D) OTHER INFORMATION: /note= "This position is C* =
                5-propynyl cytosine."

(ix) FEATURE:
            (A) NAME/KEY: modified_base
            (B) LOCATION: 6
            (D) OTHER INFORMATION: /note= "This position is U* =
                5-propynyl uracil."

(ix) FEATURE:
            (A) NAME/KEY: modified_base
            (B) LOCATION: 7
            (D) OTHER INFORMATION: /note= "This position is U* =
                5-propynyl uracil."

(ix) FEATURE:
            (A) NAME/KEY: modified_base
            (B) LOCATION: 8
            (D) OTHER INFORMATION: /note= "This position is U* =
                5-propynyl uracil."

(ix) FEATURE:
            (A) NAME/KEY: modified_base
            (B) LOCATION: 9
            (D) OTHER INFORMATION: /note= "This position is U* =
                5-propynyl uracil."

(ix) FEATURE:
            (A) NAME/KEY: modified_base
            (B) LOCATION: 10
            (D) OTHER INFORMATION: /note= "This position is U* =
                5-propynyl uracil."

(ix) FEATURE:
            (A) NAME/KEY: modified_base
            (B) LOCATION: 11
            (D) OTHER INFORMATION: /note= "This position is U* =
                5-propynyl uracil."

(xi) SEQUENCE DESCRIPTION: SEQ ID NO:19:

NNNNANNNNN N                                                                11

(2) INFORMATION FOR SEQ ID NO:20:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 1
            (D) OTHER INFORMATION: /note= "This position is C* =
                5-propynyl cytosine."

(ix) FEATURE:
            (A) NAME/KEY: modified_base
            (B) LOCATION: 2
            (D) OTHER INFORMATION: /note= "This position is U* =
                5-propynyl uracil."

(ix) FEATURE:
            (A) NAME/KEY: modified_base
            (B) LOCATION: 3
            (D) OTHER INFORMATION: /note= "This position is U* =
                5-propynyl uracil."

(ix) FEATURE:
            (A) NAME/KEY: modified_base
            (B) LOCATION: 4
            (D) OTHER INFORMATION: /note= "This position is C* =
                5-propynyl cytosine."

(ix) FEATURE:
            (A) NAME/KEY: modified_base (B) LOCATION: 6
                    (D) OTHER INFORMATION: /note= "This position is U* =
                        5-propynyl uracil."

(ix) FEATURE:
                    (A) NAME/KEY: modified_base
                    (B) LOCATION: 7
                    (D) OTHER INFORMATION: /note= "This position is U* =
                        5-propynyl uracil."

(ix) FEATURE:
                    (A) NAME/KEY: modified_base
                    (B) LOCATION: 8
                    (D) OTHER INFORMATION: /note= "This position is U* =
                        5-propynyl uracil."

(ix) FEATURE:
                    (A) NAME/KEY: modified_base
                    (B) LOCATION: 9
                    (D) OTHER INFORMATION: /note= "This position is U* =
                        5-propynyl uracil."

(xi) SEQUENCE DESCRIPTION: SEQ ID NO:20:

CNNNANNNN                                                                              9

(2) INFORMATION FOR SEQ ID NO:21:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ix) FEATURE:
                    (A) NAME/KEY: modified_base
                    (B) LOCATION: 1
                    (D) OTHER INFORMATION: /note= "This position is U* =
                        5-propynyl uracil."

(ix) FEATURE:
                    (A) NAME/KEY: modified_base
                    (B) LOCATION: 2
                    (D) OTHER INFORMATION: /note= "This position is U* =
                        5-propynyl uracil."

(ix) FEATURE:
                    (A) NAME/KEY: modified_base
                    (B) LOCATION: 4
                    (D) OTHER INFORMATION: /note= "This position is U* =
                        5-propynyl uracil."

(ix) FEATURE:
                    (A) NAME/KEY: modified_base
                    (B) LOCATION: 5
                    (D) OTHER INFORMATION: /note= "This position is U* =
                        5-propynyl uracil."

(ix) FEATURE:
                    (A) NAME/KEY: modified_base
                    (B) LOCATION: 7
                    (D) OTHER INFORMATION: /note= "This position is U* =
                        5-propynyl uracil."

(ix) FEATURE:
                    (A) NAME/KEY: modified_base
                    (B) LOCATION: 8
                    (D) OTHER INFORMATION: /note= "This position is C' = 5
                        methyl cytosine."

(ix) FEATURE:
                    (A) NAME/KEY: modified_base
                    (B) LOCATION: 9
                    (D) OTHER INFORMATION: /note= "This position is U* =
                        5-propynyl uracil."

(ix) FEATURE:
                    (A) NAME/KEY: modified_base

-continued

```
        (B) LOCATION: 10
        (D) OTHER INFORMATION: /note= "This position is U* =
            5-propynyl uracil."

(ix) FEATURE:
        (A) NAME/KEY: modified_base
        (B) LOCATION: 11
        (D) OTHER INFORMATION: /note= "This position is C' = 5
            methyl cytosine."

(ix) FEATURE:
        (A) NAME/KEY: modified_base
        (B) LOCATION: 12
        (D) OTHER INFORMATION: /note= "This position is U* =
            5-propynyl uracil."

(ix) FEATURE:
        (A) NAME/KEY: modified_base
        (B) LOCATION: 13
        (D) OTHER INFORMATION: /note= "This position is U* =
            5-propynyl uracil."

(ix) FEATURE:
        (A) NAME/KEY: modified_base
        (B) LOCATION: 14
        (D) OTHER INFORMATION: /note= "This position is C' = 5
            methyl cytosine."

(ix) FEATURE:
        (A) NAME/KEY: modified_base
        (B) LOCATION: 15
        (D) OTHER INFORMATION: /note= "This position is U* =
            5-propynyl uracil."

(ix) FEATURE:
        (A) NAME/KEY: modified_base
        (B) LOCATION: 16
        (D) OTHER INFORMATION: /note= "This position is U* =
            5-propynyl uracil."

(ix) FEATURE:
        (A) NAME/KEY: modified_base
        (B) LOCATION: 17
        (D) OTHER INFORMATION: /note= "This position is U* =
            5-propynyl uracil."

(ix) FEATURE:
        (A) NAME/KEY: modified_base
        (B) LOCATION: 18
        (D) OTHER INFORMATION: /note= "This position is U* =
            5-propynyl uracil."

(ix) FEATURE:
        (A) NAME/KEY: modified_base
        (B) LOCATION: 19
        (D) OTHER INFORMATION: /note= "This position is C' = 5
            methyl cytosine."

(ix) FEATURE:
        (A) NAME/KEY: modified_base
        (B) LOCATION: 20
        (D) OTHER INFORMATION: /note= "This position is U* =
            5-propynyl uracil."

(xi) SEQUENCE DESCRIPTION: SEQ ID NO:21:

NNANNANNNN NNNNNNNNNN                                              20
```

ENHANCED TRIPLE-HELIX AND DOUBLE-HELIX FORMATION DIRECTED BY OLIGONUCLEOTIDES CONTAINING MODIFIED PYRIMIDINES

This is a continuation of application Ser. No. 07/935,444 filed on Aug. 25, 1992 now abandoned.

This is a continuation-in-part of U.S. patent application Ser. No. 799,824, filed Nov. 26, 1991 now U.S. Pat. No. 5,484,908 and incorporated herein by reference.

TECHNICAL FIELD

The invention relates generally to novel nucleosides and oligonucleotide analogs, and to oligonucleotide-based diagnosis by binding of the oligonucleotide analogs to single or double-stranded nucleic acid target sequences. More specifically, the invention concerns oligomers containing 5-substituted cytosine and uracil base residues and intermediates in their synthesis.

BACKGROUND ART

Sequence-specific binding of oligonucleotides both to single-stranded and to duplex DNA has been recognized. The appropriate sequence recognition for binding to single-stranded targets is well known: the A-T and G-C pairing characteristic of duplex formation has been established as the basis for DNA replication and transcription. More recently, it has been realized that oligonucleotides may also bind in a sequence-specific manner to duplex DNA in order to form triplexes.

Thus, duplex DNA can be specifically recognized by oligomers based on a recognizable nucleotide sequence. Two major recognition motifs have been recognized. In an earlier description of a "CT" motif, cytosine residues recognize G-C basepairs while thymine residues recognize A-T basepairs in the duplex. These recognition rules are outlined by Maher III, L. J., et al., *Science* (1989) 245:725–730; Moser, H. E., et al., *Science* (1987) 238:645–650. More recently, an additional motif, called "GT" recognition, was described by Cooney, M., et al., *Science* (1988) 241:456–459; Hogan, M. E., et al., EP Publication 375408. In the G-T motif, A-T pairs are recognized by adenine or thymine residues and G-C pairs by guanine residues.

In both of these binding motifs, the recognition sequence must align with a sequence as played out on one of the chains of the duplex; thus, recognition, for example, of an A-T pair by a thymine depends on the location of repeated adenyl residues along one chain of the duplex and thymine series on the other. The recognition does not extend to alternating A-T-A-T (SEQ ID NO: 1) sequences; only the adenyl residues on one chain or the other would be recognized. An exception to the foregoing is the recent report by Griffin, L. C., et al., Science (1989) 245:967–971, that limited numbers of guanine residues can be provided within pyrimidine-rich oligomers and specifically recognize thymine-adenine base pairs; this permits the inclusion of at least a limited number of pyrimidine residues in the homopurine target.

The two motifs exhibit opposite binding orientations with regard to homopurine target chains in the duplex. In the CT motif, the targeting oligonucleotide is oriented parallel to the target purine-rich sequence; in the GT motif, it is oriented antiparallel (Beal, P. A., et al., *Science* (1990) 251:1360–1363). Thus, recognition sequences in the CT motif are read with respect to target 5'→3' sequences so that in the 5'→3' direction, synthetic oligonucleotides contain the required sequence of C or T residues with respect to the guanine or adenyl residues in the target. In the GT motif, on the other hand, the targeted sequence is read 5'→3' in order to design the 3'→5' sequence of the targeting oligonucleotide.

One problem that has arisen with respect to binding in the CT system resides in the ionization state of the "C" residue at neutral or physiological pH. In order to form the appropriate hydrogen bond donor/acceptor pattern, the amino group at position 3 of the C must be protonated. This is consonant with the $pK_a$ when the pH is low (cytosine $pK_a$ is 4.25), but at neutral pH, most of the pyrimidines are unprotonated. This interferes with binding at physiological pH.

One proposed solution to this problem has been the use of 5-methylcytosine ($pK_a$ 4.35) instead of cytosine as the recognizing "C". This approach was based upon the observation (Lee, J. S. et al., *Nucleic Acids Res* (1984) 12:6603–6614) that polypyrimidine oligonucleotides composed of 5-methyldeoxycytidine can bind to poly G:poly C double-stranded DNA at neutral pH. The ability of both 5-bromouracil and 5-methylcytosine to bind duplex DNA at the same homopurine target sequence as their T/C analogs, but with greater affinities and over an extended Ph range has also been reported by Povsic, T. J., et al., *J Am Chem Soc* (1989) 111:3059–3061. The improved binding of 5-methylcytosine compared to cytosine in CT mode binding is believed to result from (i) an increased $pK_a$, and (ii) interaction of the methyl group at position 5 with adjacent methyl groups in the oligomer. Another approach which was taken (Cooney, M.; Czernuszewicz, G.; Postel, E. H.; Flint, E. S. J.; and Hogan, M. E. *Science* (1988) 241:456–459) was the substitution of deoxyguanosine for deoxycytidine, and the substitution of deoxyadenosine for thymidine to yield an alternative binding motif.

Sequence-specific targeting of both single-stranded and duplex oligonucleotides has applications in diagnosis, analysis, and therapy. Under some circumstances wherein such binding is to be effected, it is advantageous to stabilize the resulting duplex or triplex over long time periods.

Covalent crosslinking of the oligomer to the target provides one answer to this problem. Sequence-specific recognition of single-stranded DNA accompanied by covalent crosslinking has been reported by several groups. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., crosslinking agent. Administration to a live subject does not readily admit of this mechanism of action.

In addition, Vlassov, V. V. et al., *Gene* (1988) 313–322 and Fedorova, O. S. et al., *FEBS* (1988) 228:273–276, describe targeting duplex DNA with a 5'-phospho-linked oligonucleotide.

In effecting binding to obtain a triplex, to provide for instances wherein purine residues are concentrated on one chain of the target and then on the opposite chain, oligonucleotides of inverted polarity may be provided. By "inverted polarity" is meant that the oligonucleotide contains tandem sequences which have opposite polarity, i.e., one having polarity 5'→3' followed by another with polarity 3'→5', or vice versa. This implies that these sequences are joined by linkages which can be thought of as effectively a 3'—3' internucleotide junction (however the linkage is accomplished), or effectively a 5'—5' internucleotide junction. Such oligomers have been suggested as by-products of reactions to obtain cyclic oligonucleotides by Capobionco, M. L., et al., *Nucleic Acids Res* (1990) 18:2661–2669. Compositions of "parallel-stranded DNA" designed to form hairpins secured with AT linkages using either a 3'—3' inversion or a 5'—5' inversion have been synthesized by van de Sande, J. H., et al., *Science* (1988) 241:551–557. In addition, triple helix formation using an oligomer which contains an effective 3'—3' linkage has been described by Horne, D. A., and Dervan, P. B., *J Am Chem Soc* (1900) 112:2435–2437.

Single-stranded nucleic acid, primarily RNA, is the target molecule for oligonucleotides that are used to inhibit gene expression by an "antisense" mechanism (Uhlmann, E., et al, *Chem Reviews* (1990) 90:543–584; van der Krol, A. R., et al, *Biotechniques* (1988) 6:958–976). Antisense oligonucleotides are postulated to exert an effect on target gene expression by hybridizing with a complementary RNA sequence. The hybrid RNA-oligonucleotide duplex appears to interfere with one or more aspects of RNA metabolism including processing, translation and metabolic turnover. Chemically modified oligonucleotides have been used to enhance their nuclease stability.

DISCLOSURE OF THE INVENTION

The invention provides oligomers containing a multiplicity of nucleotides wherein at least one nucleotide comprises a 5-substituted uracil or cytosine residue. oligomers including these modified bases show enhanced binding capacities in the formation of duplexes or triplexes with single-stranded or duplex oligonucleotide targets, respectively. The substitution of 5-alkenyl-, alkynyl- or aryl-substituted uracil residues for thymine in oligomers which target DNA duplexes enhances the binding affinity. Substitution of thymine residues by the 5-substituted uracil residues of the invention or substitution of cytosine residues by the 5-substituted cytosine residues of the invention enhance the ability of the resulting oligomer to bind single-stranded DNA or RNA targets.

The ability of the 5-substituted pyrimidine residues of the invention to enhance affinity of the oligomer for single-stranded and duplex targets permits modifications to the oligomer in which they are contained. These modifications may diminish affinity, but confer other useful properties such as stability to nuclease cleavage, ability to permeate cell membranes, *Biochemistry* (1988) 27:3197–3203. Use of crosslinking in triple-helix forming probes was also disclosed by Home, et al., *J Am Chem Soc* (1990) 112:2435–2437.

Use of $N^4,N^4$-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674. These papers also describe the synthesis of oligonucleotides containing the derivatized cytosine. Matteucci and Webb, in a later article in *Tetrahedron Letters* (1987) 28:2469–2472, describe the synthesis of oligomers containing $N^6,N^6$-ethanoadenine and the crosslinking properties of this residue in the context of an oligonucleotide binding to a single-stranded DNA.

In a recent paper, Praseuth, D., et al., *Proc Natl Acad Sci (USA)* (1988) 85:1349–1353, described sequence-specific binding of an octathymidylate conjugated to a photoactivatable crosslinking agent to both single-stranded and double-stranded DNA. A target 27-mer duplex containing a polyA tract showed binding of the octathymidylate in parallel along the polyA. Photoactivated crosslinking of the duplex with a p-azidophenacyl residue covalently linked to the terminus of the octathymidylate was achieved. While sequence-specific association occurred at the predicted region of the duplex, it appeared that the crosslinking reaction itself was not target specific. As photoactivation was required to form the covalent crosslink, there could be no question of accurate sequence-specific association of the octathymidylate to the target sequence in the 27-mer duplex. A requirement for photoactivation, however, seriously limits the therapeutic potential of the and the like. The decrease in affinity resulting from the modifications is acceptable because of the enhanced affinity conferred by the 5-substituted pyrimidine. Thus, particularly preferred oligomers of the invention contain modified internucleoside linkages and/or modified sugars, as well as the 5-substituted pyrimidine bases of the invention.

Accordingly, in one aspect, the invention is directed to an oligomer comprising a multiplicity of nucleotides wherein at least one said nucleotide comprises a base of the formula:

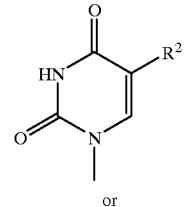

(1)

or

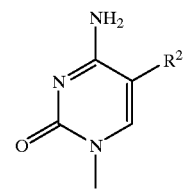

(2)

wherein $R^2$ is selected from the group consisting of propynyl (—C≡C—CH₃), propenyl (—CH=CH—CH₃), 3-buten-1-yneyl (—C≡C—CH=CH₂), 3-methyl-1-butynyl (—C≡C—CH(CH₃)2), 3,3-dimethyl-1-butynyl (—C≡C—C(CH₃)₃), 1-butynyl, 1-pentadiynyl, ethynyl, vinyl, bromovinyl, phenylethynyl, o-, m-, and p-pyridine-ethynyl, 2-, 4- and 5-pyrimidine-ethynyl, triazine-ethynyl, arylethynyl, phenyl, 2-thiazolyl, 1-methyl-2-imidazolyl, 2-imidazolyl, 2-isoxazolyl, m-pyridinyl, p-pyridinyl and o-pyridinyl.

In other aspects, the invention is directed to duplexes or triplexes obtained by binding the foregoing oligomers to single-stranded or duplex targets.

In other aspects, the invention is directed to intermediates in the synthesis of the oligomers of the invention, including nucleoside analogs of the formula:

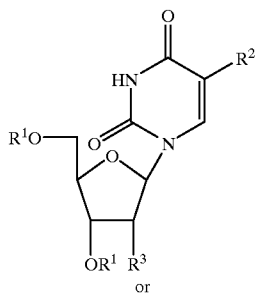

(4)

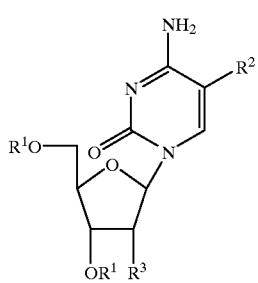

(5)

wherein each $R^1$ is independently H or a blocking group;

$R^2$ is selected from the group consisting of propynyl, 3-buten-1-yl, 3-methyl-1-butynyl, 3,3-dimethyl-1-butynyl, propenyl, 1-pentadiynyl, 1-butynyl, ethynyl, vinyl, bromovinyl, phenylethynyl, o-, m-, and p-pyridine-ethynyl, 2-, 4- and 5-pyrimidine-ethynyl, triazine-ethynyl and arylethynyl, phenyl, 2-thiazoyl, 1-methyl-2-imidazolyl, 2-imidazolyl, 2-isoxazolyl, o-pyridinyl, m-pyridinyl and p-pyridinyl; and $R^3$ is selected from the group consisting of H, OH, F, OR or SR, wherein R is allyl or alkyl(1–3C), with the proviso that if $R^3$ is H or OH, and both $R^1$ are H, $R^2$ cannot be propynyl.

Other useful intermediates in the synthesis of the oligomers of the invention include an o-xyloso nucleoside dimer having the general structural formula:

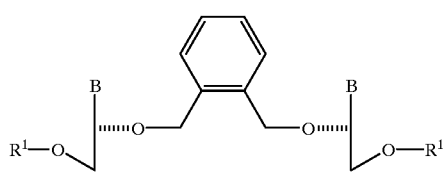

(6)

wherein each $R^1$ is H or a blocking group; and each B is independently a purine or pyrimidine base, provided that at least one B is

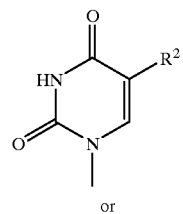

(1)

or

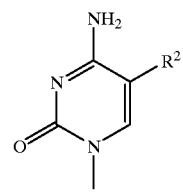

(2)

wherein $R^2$ is as defined above.

Also included are intermediates of the formula:

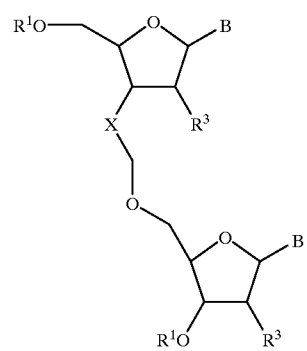

(8)

wherein

X is selected from the group consisting of O and S;

B is independently a purine or pyrimidine base, provided that at least one B is

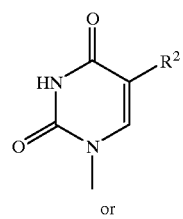

(1)

or

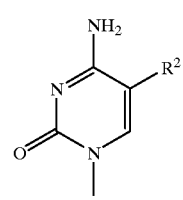

(2)

wherein
  each $R^1$ is independently selected from the group consisting of H and a blocking group;
  each $R^2$ is independently selected from the group consisting of propynyl, 3-buten-1-yneyl, 3-methyl-1-butynyl, 3,3-dimethyl-1-butynyl, propenyl, 1-pentadiynyl, 1-butynyl, ethynyl, vinyl, bromovinyl, phenylethynyl, o-, m-, and p-pyridine-ethynyl, 2-, 4- and 5-pyrimidine-ethynyl, trazine-ethynyl and arylethynyl, phenyl, 2-thiazoyl, 1-methyl-2-imidazolyl, 2-imidazoyl, 2-isoxazolyl, o-pyridinyl, m-pryridinyl and p-pyridinyl; and each $R^3$ is independently selected from the group consisting of H, OH, F, OR and SR, wherein each R is independently allyl or alkyl (1–3C).

Also included are oligomers containing one or more modified linkages such as sulfide or sulfone linkages (Benner, S. A., international publication number WO 89/12060), riboacetal and related linkages, amide linkages and 2',5' internucleotide linkages described in commonly owned pending U.S. application Ser. Nos. 07/806,710, 07/899,736, 07/894,397 and 07/892,902. Each cited reference is incorporated herein by reference.

Other aspects of the invention are directed to methods of detecting the presence, absence or amount of a particular single-stranded DNA or RNA or a particular target duplex in a biological sample using the oligomers of the invention.

A feature of the invention is that the oligomers of the invention can be comprised of a variety of different sequences and thereby used to target a variety of different single-stranded or double-stranded target sequences.

An advantage of the present invention is that the oligomers of the invention are capable of forming triplexes under physiological pH.

Another advantage of oligomers containing 5-$R^2$ substituted uracil or cytosine compared to oligomers containing thymine or cytosine is that the lipophilic group ($R^2$) may enhance cell permeation or uptake. The nucleosides containing these bases are more lipophilic than uridine, cytidine or thymidine based on retention times on HPLC.

MODES OF CARRYING OUT THE INVENTION

It has been found that the oligomers of the invention have enhanced binding properties with respect to complementary single-stranded and double-stranded nucleic acid sequences as compared to unmodified oligomers. Triple helix structures can be formed at physiological Ph levels of 7.0 and higher, where unmodified control oligomers were less efficient. Improved duplex formation is also noted. The oligomers of the present invention are generally characterized as containing one or more pyrimidines modified at position 5. Preferred are modified C and U. The oligomers may also contain additional modifications in nucleotides that contain these 5-modified pyrimidines or in other nucleotides that comprise the oligomer. An exemplary list of such modifications include oligomers where (i) one or more nucleotide residues are modified at the 2' position, (ii) one or more crosslinking moieties have been incorporated, (iii) switchback linkers have been incorporated, (iv) substitute internucleotide linkages have been included and (v) other base analogs that facilitate triplex formation, such as 8-hydroxy-$N^6$-methyladenine, have been included. One or more of such modifications may advantageously be incorporated into a given oligomer depending on target nucleic acid sequences.

Substitution of 5-$R^2$ substituted U for T in oligomers results in enhanced ability to form triplexes and duplexes as compared with the oligomers containing thymine. These oligomers, in triplex formation, appear to recognize adenine residues in adenine-thymine base pairs and bind in the parallel CT triplex motif. Oligomers containing 5-$R^2$-C in place of C bind duplex DNA, but not as well as control oligomers containing 5-methylcytosine at corresponding positions. The reduced efficiency of triplex formation is believed to result primarily from the reduced Pka of the substituted base. In the 5'propynyl-substituted nucleoside corresponding to the nucleoside containing 5-methylcytosine, the Pka is only 3.30. The oligomers of the invention are thus capable of forming triplexes with various target sequences such as HER-2 and HIV sequences by coupling into the major groove of a target DNA duplex under physiological pH.

However, alteration of the heterocycle Pka as described above for the 5-$R^2$-C does not significantly affect binding to single-stranded target nucleic acid. In addition to binding efficiently to double-stranded target sequences, oligomers of the invention containing 5-$R^2$ substituted U in place of T and/or 5-$R^2$ substituted C in place of C were also found to bind single-stranded RNA efficiently. Oligomers containing either 5-$R^2$-C or 5-$R^2$-U formed duplex structures with complementary single-stranded RNA that had increased thermal stability (T) compared to the duplex formed by a control oligomer as described below. The novel oligomers of the present invention are therefore also useful wherein a selected RNA sequence is bound. The oligomers of the invention may be constructed to have any desired sequence. Compositions of the invention can be used for diagnostic purposes in order to detect the presence of neoplastic growth, viruses and a variety of disease conditions.

The oligomers of the invention are also suitable for binding to target sequences via GT motif binding.

Definitions:

As used herein "oligonucleotide" or "oligomer" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base.

The oligomers of the invention may be formed using conventional phosphodiester-linked nucleotides and synthesized using standard solid phase (or solution phase) oligonucleotide synthesis techniques, which are now commercially available. However, the oligomers of the invention may also contain one or more "substitute" linkages as is generally understood in the art. These "substitute" linkages are defined herein as conventional alternative linkages such as phosphorothioate, methylphosphonate, dithioate, riboacetal, 2',5' linkages, amide linkages, alkylphosphonates or phosphoramidate (methoxyethylamine and the like), are synthesized as described in the generally available literature and in references cited herein (WO 90/15065). Substitute linkages that may be used in the oligomers disclosed herein also include nonphosphorous based internucleotide linkages such as the 3'-thioformacetal (—S—$CH_2$—O—), formacetal (—O—$CH_2$—O—) and 3'-amine (—NH—$CH_2$—$CH_2$—) internucleotide linkages disclosed and claimed in commonly owned pending U.S. patent application Ser. Nos. 690,786 and 763,130, both incorporated herein by reference. Substitute linkage(s) may be utilized in the oligomers in order to further facilitate binding with complementary target nucleic acid sequences or to increase the stability of the oligomers toward nucleases.

The term "nucleoside" or "nucleotide" will similarly be generic to ribonucleosides or ribonucleotides, deoxyribonucleosides or deoxyribonucleotides, or to any other nucleoside which is an N-glycoside or C-glycoside of a purine or pyrimidine base, or modified purine or pyrimidine base. Thus, the stereochemistry of the sugar carbons may be other than that of D-ribose in one or more residues. Also included are analogs where the ribose or deoxyribose moiety is replaced by an alternate structure such as the 6-member morpholino ring described in U.S. Pat. No. 5,034,506. The enhanced efficiency of binding by oligomers containing the base analogs of the present invention is believed to be primarily a function of the base alone. Because of this, elements ordinarily found in oligomers, such as the furanose ring or the phosphodiester linkage may be replaced with any suitable functionally equivalent element.

"Nucleosides" or "nucleotides" also include those which contain modifications in the sugar moiety, for example, wherein one or more of the hydroxyl groups are replaced with halogen, aliphatic groups, or functionalized as ethers, amines, and the like.

Furthermore, as the α anomer binds to duplexes in a manner similar to that for the β anomers, one or more nucleotides may contain this linkage or a domain thereof. (Praseuth, D., et al., *Proc Natl Acad Sci* (USA) (1988) 85:1349–1353). Anomeric oligomers containing the 5-$R^2$ substituted pyrimidines described herein represent a class of modified oligomers included in the present invention. "Nucleoside" and "nucleotide" include those moieties which contain not only the known purine and pyrimidine bases, but also heterocyclic bases which have been modified. Such modifications include alkylated purines or pyrimidines, acylated purines or pyrimidines, or other heterocycles. Such "analogous purines" and "analogous pyrimidines" are those generally known in the art, many of which are used as chemotherapeutic agents. An exemplary but not exhaustive list includes $N^4,N^4$-ethanocytosine, 7-deazaxanthosine, 7-deazaguanosine, 8-hydroxy-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, $N^6$-isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, beta-D-mannosylqueosine, 5'-methoxycarbonylmethyluracil, 5-methoxyuracil, 2-methylthio-$N^6$-isopentenyladenine, uracil-5-oxyacetic acid methyl ester, pseudouracil, 5-methyl-2-thiouracil, 2-thiouracil, 4-thiouracil, 5-methyluracil, uracil-5-oxyacetic acid, queosine, 2-thiocytosine, and 2,6-diaminopurine.

Preferred bases are adenine, guanine, thymine, cytosine, 5-methylcytosine, 7-deazaxanthosine and 7-deazaguanosine. Synthesis and use of oligomers containing 7-deazaxanthosine and 7-deazaguanosine is described in commonly owned pending U.S. application Ser. No. 07/787,920, which reference is incorporated herein by reference.

The oligomers of the present invention may be of any length, but lengths of greater than or equal to about 7 nucleotides, and preferably greater than about 10, are preferred. However, the longer oligonucleotides may also be made, particularly those of greater than 50 nucleotides or greater than 100 nucleotides. oligonucleotides may contain conventional internucleotide phosphodiester linkages or may contain modified forms such as phosphoramidate linkages. These alternative linking groups include, but are not limited to embodiments wherein a moiety of the formula P(O)S, ("thioate"), P(S)S ("dithioate"), P(O)NR'$_2$, P(O)R', P(o)OR$^6$, Co, or CONR'$_2$, wherein R' is H (or a salt) or alkyl (1–12C) and R$^6$ is alkyl (1–9C) is joined to adjacent nucleotides through —O— or —S—. Dithioate linkages are disclosed in commonly owned U.S. application Ser. No. 248,517, incorporated herein by reference. Particularly preferred linkages for use in the oligomers of the present invention include thioate linkages and methylphosphonate linkages. These linkages confer added stability on the oligomer in physiological environments. While not all such linkages in the same oligomer need to be identical, particularly preferred oligomers of the invention contain uniformly thioate linkages or uniformly methylphosphonate linkages.

Also included are "derivatives" of oligonucleotides. "Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be derivatized through any convenient linkage. For example, intercalators, such as acridine can be linked through any available —OH or —SH, e.g., at the terminal 5' position of RNA or DNA, the 2' positions of RNA, or an OH, NH$_2$, COOH or SH engineered into the 5 position of pyrimidines, e.g., instead of the 5 methyl of thymine, a derivatized form which contains, for example, —CH$_2$CH$_2$NH$_2$, —CH$_2$CH$_2$CH$_2$OH or —CH$_2$CH$_2$CH$_2$SH in the 5 position. A wide variety of substituents can be attached, including those bound through conventional linkages. The indicated —OH moieties in the oligomers may be replaced by phosphonate groups, protected by standard protecting groups, or activated to prepare additional linkages to other nucleotides, or may be bound to the conjugated substituent. The 5' terminal OH may be phosphorylated; the 2'-OH or OH substituents at the 3' terminus may also be phosphorylated. The hydroxyls may also be derivatized to standard protecting groups.

Among the most preferred derivatives of the oligomers of the invention are the 2'-O-allyl derivatives. The presence of the 2'-O-allyl groups appears to enhance permeation ability and stability to nuclease degradation, but does not appear to diminish the affinity of the oligomer for single chain or duplex targets.

Oligonucleotides or the segments thereof of are conventionally synthesized. Methods for such synthesis are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578.

In addition to employing these very convenient and now most commonly used, solid phase synthesis techniques, oligonucleotides may also be synthesized using solution phase methods such as triester synthesis. These methods are workable, but in general, less efficient for oligonucleotides of any substantial length.

Preferred Embodiments:

One group of oligomers of the present invention can be represented by the formula:

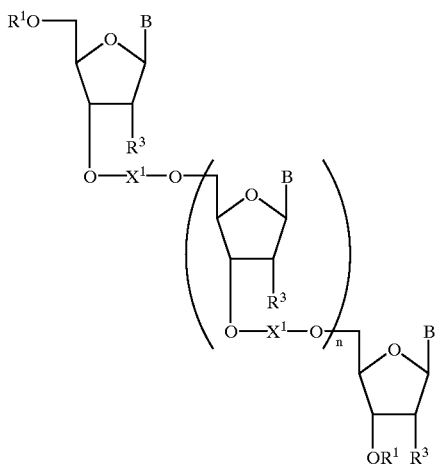

(3)

wherein
each $R^3$ is independently selected from the group consisting of H, OH, F, $OCH_3$, $OC_2H_5$, $OC_3H_7$, $SCH_3$, $SC_2H_5$, $SC_3H_7$, $OC_3H_5$, and $SC_3H_5$;
each $R^4$ is independently selected from the group consisting of H, and a blocking group;
n is an integer from 4 to 30; and
B is a purine or pyrimidine base, provided that at least one B is

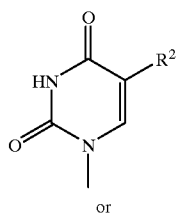

(1)

or

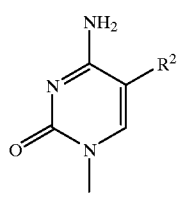

(2)

wherein $R^2$ is selected from the group consisting of propynyl, 3-buten-1-yneyl, 3-methyl-1-butynyl, 3,3-dimethyl-1-butynyl, propenyl, 1-pentadiynyl, 1-butynyl, ethynyl, vinyl, bromovinyl, phenylethynyl, o-, m-, and p-pyridine-ethynyl, 2-, 4- and 5-pyrimidine-ethynyl, triazine-ethynyl and arylethynyl, phenyl, 2-thiazoyl, 1-methyl-2-imidazolyl, 2-imidazolyl, 2-isoxazolyl, o-pyridinyl, m-pyridinyl and p-pyridinyl; and wherein each $X^1$ is independently —P(S)O—, —P(O)O— or —P(Me)O—.

However, other preferred oligomers of the invention contain linkages other than phosphodiesters. Particularly useful forms of these linkages include riboacetal, phosphorothioate, methyl phosphonate, formacetal, 3'-thioformacetal and 2',5' linkages (such as 2',5' carbamate, 5',2' carbamate, 5',2' methylcarbamate or 5',2' thioformacetal linkages disclosed in pending U.S. application Ser. No. 07/892,902, incorporated herein by reference). For synthesis of oligomers containing formacetal-type linkages in lieu of at least some phosphodiester linkages, dimeric synthons of the formula:

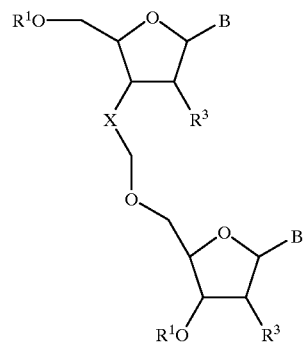

(8)

wherein the substituents B, X, $R^1$ and $R^3$ are as defined above are particularly useful. The foregoing synthon is obtained by first preparing the 5-iodo pyrimidine forms of B and then converting these to 5-propyne derivatives, for example, by treating the dimer synthon with propyne in the presence of palladium, CuI, triethylamine, and DMF. These synthons can be incorporated into an oligomer backbone using standard phosphodiester synthesis techniques. Synthesis of formacetal and 3'-thioformacetal linkages is described in commonly owned pending U.S. application Ser. Nos. 07/874,334 and 07/690,786, which references are incorporated herein by reference. Trimer synthons containing formacetal, 3'-thioformacetal, riboacetal or other substitute linkages are also preferred compounds. Trimers are preferred for synthesis of oligomers having enhanced permeation across cell membranes.

Particularly preferred are oligomers with methylphosphonate or thioate linkages. These linkages enhance the nuclease stability of the oligomers; their negative impact on affinity is compensated by the inclusion of the 5-substituted pyrimidines of the invention.

The synthesis of oligomers containing methylphosphonate and phosphorothioate linkages is effected using art-known modifications of standard solid-phase oligonucleotide synthesis techniques. A description of such modifications useful in thioate linkage oligomers synthesis are found, for example, in EP publication 288,163; wherein the oxidation step in solid phase automated synthesis using B-cyanoethyl phosphoramidite chemistry can be independently adjusted at any step to obtain the thioate. An alternate method for synthesis of oligomers with phosphorothioate linkages via phosphonate chemistry has also been described (Froehler, B., et al., *Nucleic Acid Res* (1986) 14:5399–5467; Froehler, B., *Tetrahedron Letters* (1986) 27:5575–5578). Synthesis of the methylphosphonate linked oligomers via methyl phosphonamidite chemistry is described (Agrawal, S. et al., *Tetrahedron Letters* (1987) 28:3539–3542).

In an additional preferred modification of the oligomers of the invention, 2'-O-allyl forms of the nucleosides containing the 5-substituted pyrimidines of the invention are included in the oligomer. 2'-O-allyl-substituted nucleosides may also be used at other positions in the oligomer. The 2'-O-allyl nucleosides can be prepared using standard methods; set-forth below is a method for synthesis of the 2'-O-allylderivatized nucleosides containing the invention pyrimidines through a common intermediate. Thus, for example, 5-propynyluridine is first protected at the 5' and 3' positions using a tetraisopropyldisiloxane reagent, and then at the 4-oxy position using ortho-nitrophenol. The protected nucleoside is then converted to the 2'-O-allyl derivative with allyl ethyl carbonate; this intermediate is alternatively converted to the 2'-O-allyl-derivatized 5-propynyluridine or the counterpart 2'-O-allyl-5'-propynylcytidine. The sequence of reactions for this conversion are outlined below in Reaction Scheme 1.

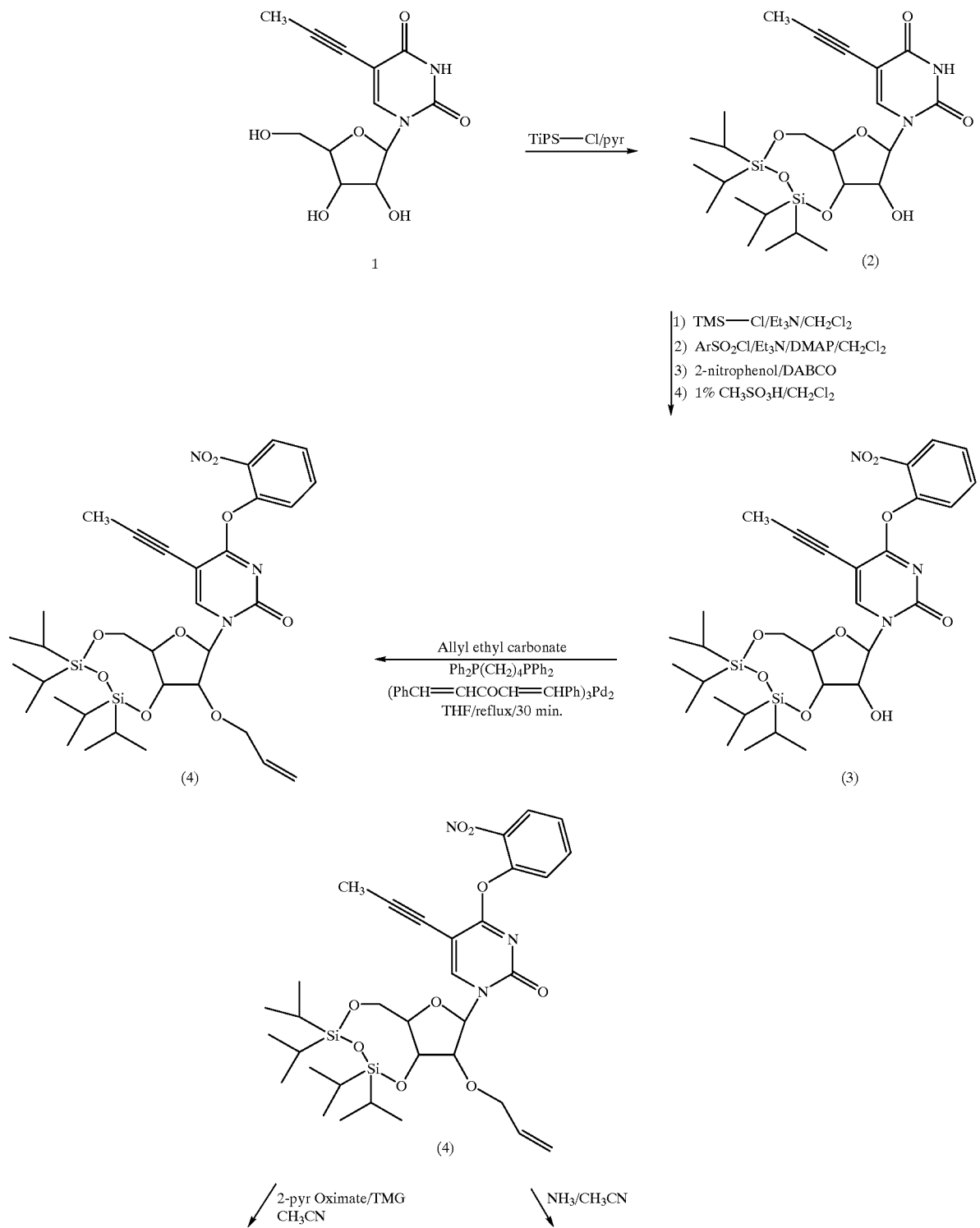

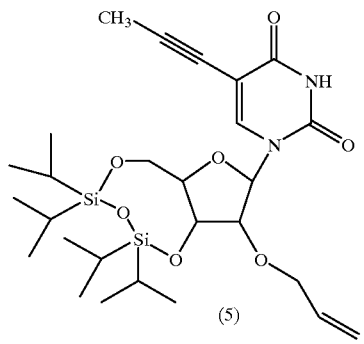

(5)

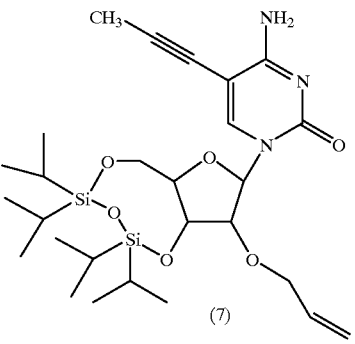

(7)

1) TBAF/THF/EtOAc
2) DMT—Cl/Pyridine

1) Formamide acetal
2) TBAF/THF/EtOAc
3) DMT—Cl/Pyridine

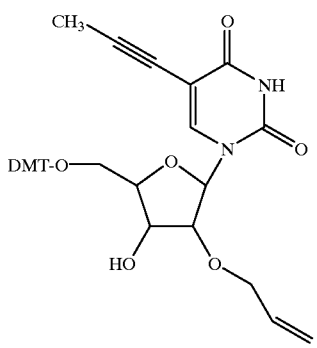

paU, 6

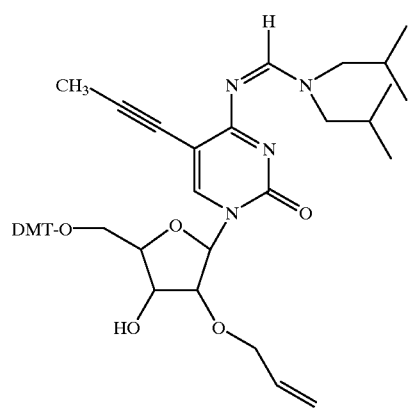

paC, 8

The nucleosides derivatized at the 2'-position can be incorporated into oligomers in the same manner as underivatized forms.

Further modifications of the resulting oligomers are described below.

Covalent Bonding Moiety

Included in some of the oligomers of the invention is a moiety which is capable of effecting at least one covalent bond between the oligomer and the duplex. Multiple covalent bonds can also be formed by providing a multiplicity of such moieties. The covalent bond is preferably to a base residue in the target strand, but can also be made with other portions of the target, including the saccharide or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand.

The crosslinking moiety can conveniently be placed as an analogous pyrimidine or purine residue in the sequence of the oligomer. The placement can be at the 5' and/or 3' ends, the internal portions of the sequence, or combinations of the above. Placement at the termini to permit enhanced flexibility is preferred. Analogous moieties can also be attached to peptide backbones.

In one preferred embodiment of the invention, a switchback oligonucleotide containing crosslinking moieties at either end can be used to bridge the strands of the duplex with at least two covalent bonds. In addition, nucleotide sequences of inverted polarity can be arranged in tandem with a multiplicity of crosslinking moieties to strengthen the complex.

Exemplary of alkylating moieties that are useful in the invention include $N^4,N^4$-ethanocytosine and $N^6,N^6$-ethanoadenine.

It is clear that the heterocycle need not be a purine or pyrimidine; indeed the pseudo-base to which the reactive function is attached need not be a heterocycle at all. Any means of attaching the reactive group is satisfactory so long as the positioning is correct.

Inverted Polarity

In their most general form, inverted polarity oligonucleotides, that may incorporate one or more nucleotide analogs described above, contain at least one segment along their length of the formula:

$$3'\text{-----}\!\!\rightarrow 5'\text{--C--}5'\text{-----}3' \tag{1}$$

or $$5'\text{-----}\!\!\rightarrow 3'\text{--C--}3'\text{-----}5' \tag{2}$$

where -C- symbolizes any method of coupling the nucleotide sequences of opposite polarity.

In these formulas, the symbol 3' - - - 5' indicates a stretch of oligomer in which the linkages are consistently formed between the 5' hydroxyl of the ribosyl residue of the nucleotide to the left with the 3' hydroxyl of the ribosyl residue of the nucleotide to the right, thus leaving the 5' hydroxyl of the rightmost nucleotide ribosyl residue free for additional conjugation. Analogously, 5' - - - 3' indicates a stretch of oligomer in the opposite orientation wherein the linkages are formed between the 3' hydroxyl of the ribosyl residue of the left nucleotide and the 5' hydroxyl of the ribosyl residue of the nucleotide on the right, thus leaving the 3' hydroxyl of the rightmost nucleotide ribosyl residue free for additional conjugation.

The linkage, symbolized by -C-, may be formed so as to link the 5' hydroxyls of the adjacent ribosyl residues in formula (1) or the 3' hydroxyls of the adjacent ribosyl residues in formula (2), or the "-C-" linkage may conjugate other portions of the adjacent nucleotides so as to link the inverted polarity strands. "-C-" may represent a linker moiety, or simply a covalent bond.

It should be noted that if the linkage between strands of inverted polarity involves a sugar residue, either the 3' or 2' position can be involved in the linkage, and either of these positions may be in either R or S configuration. The choice of configuration will in part determine the geometry of the oligomer in the vicinity of the linkage. Thus, for example, if adjacent 3' positions are used to effect a covalent linkage, less severe deformation of the oligonucleotide chain will generally occur if both 3' hydroxyls involved in the linkage are in the conventional R configuration. If they are both in the S configuration, this will result in a favorable "kink" in the chain.

In addition to the use of standard oligonucleotide synthesis techniques or other couplings to effect the 5'—5' or 3'—3' linkage between ribosyl moieties, alternative approaches to joining the two strands of inverted polarity may be employed. For example, the two appended bases of the opposing termini of the inverted polarity oligonucleotide sequences can be linked directly or through a linker, or the base of one can be linked to the sugar moiety of the other. Any suitable method of effecting the linkage may be employed. The characterizing aspect of the switchback oligonucleotides of the invention is that they comprise tandem regions of inverted polarity, so that a region of 3'→5' polarity is followed by one of 5'→3' polarity, or vice versa, or both.

Depending on the manner of coupling the segments with inverted polarity, this coupling may be effected by insertion of a dimeric nucleotide wherein the appropriate 3' positions of each member of the dimer or the 5' positions of each member of the dimer are activated for inclusion of the dimer in the growing chain, or the conventional synthesis can be continued but using for the condensing nucleotide a nucleotide which is protected/activated in the inverse manner to that which would be employed if the polarity of the chain were to remain the same. This additional nucleotide may also contain a linker moiety which may be included before or after condensation to extend the chain.

The synthesis of oligonucleotides having modified residues and/or inverted polarity may be accomplished utilizing standard solid phase synthesis methods.

In general, there are two commonly used solid phase-based approaches to the synthesis of oligonucleotides containing conventional 3'→5' or 5'→3' linkages, one involving intermediate phosphoramidites and the other involving intermediate phosphonate linkages. In the phosphoramidite based synthesis, a suitably protected nucleotide having a cyanoethylphosphoramidite at the position to be coupled is reacted with the free hydroxyl of a growing nucleotide chain derivatized to a solid support. The reaction yields a cyanoethyl-phosphite, which linkage must be oxidized to the cyanoethylphosphate at each intermediate step, since the reduced form is unstable to acid. The H-phosphonate-based synthesis is conducted by the reaction of a suitably protected nucleoside containing an H-phosphonate moiety at a position to be coupled with a solid phase-derivatized nucleotide chain having a free hydroxyl group, in the presence of a suitable activator to obtain an H-phosphonate diester linkage, which is stable to acid. Thus, the oxidation to the phosphate or thiophosphate can be conducted at any point during the synthesis of the oligonucleotide or after synthesis of the oligonucleotide is complete. The H-phosphonates can also be converted to phosphoramidate derivatives by reaction with a primary or secondary amine in the presence of carbon tetrachloride. To indicate the two approaches generically, the incoming nucleoside is regarded as having an "activated phosphite/phosphate" group.

Variations in the type of internucleotide linkage are achieved by, for example, using the methyl phosphonate precursors rather than the H-phosphonates per se, using thiol derivatives of the nucleoside moieties and generally by methods known in the art. Nonphosphorous based linkages may also be used, such as the formacetal 3'-thioformacetal, 3'-amino and 5'-ether type linkages described above.

Thus, to obtain an oligonucleotide segment which has a 3'→5' polarity, a nucleotide protected at the 5' position and containing an activated phosphite/phosphate group at the 3' position is reacted with the hydroxyl at the 5' position of a nucleoside coupled to a solid support through its 3'-hydroxyl. The resulting condensed oligomer is deprotected and the reaction repeated with an additional 5'-protected, 3'-phosphite/phosphate activated nucleotide. Conversely, to obtain an oligomeric segment of 5'→3' polarity, a nucleotide protected in the 3' position and containing an activated phosphite/phosphate in the 5' position is reacted with a nucleotide oligomer or nucleoside attached to a solid support through the 5' position, leaving the 3'-hydroxyl available to react. Similarly, after condensation of the incoming nucleotide, the 3' group is deprotected and reacted with an additional 3'-protected, 5'-activated nucleotide. The sequence is continued until the desired number of nucleotides have been added.

In addition to employing these very convenient and now most commonly used, solid phase synthesis techniques, oligonucleotides may also be synthesized using solution phase methods such as triester synthesis. These methods are workable, but in general, less efficient for oligonucleotides of any substantial length.

This oligonucleotide chain elongation will proceed in conformance with a predetermined sequence in a series of condensations, each one of which results in the addition of another nucleotide. Prior to the addition of a nucleoside having an activated phosphite/ phosphate, the protecting group on the solid support-bound nucleotide is removed. Typically, for example, removal of the commonly-employed dimethoxytrityl (DMT) group is done by treatment with 2.5% v/v dichloroacetic acid/dichloromethane, although 1% w/v trichloroacetic acid/dichloromethane or $ZnBr_2$-saturated nitromethane, are also useful. Other deprotection procedures suitable for other protecting groups will be apparent to those of ordinary skill in the art. The deprotected nucleoside or oligonucleotide bound to solid support is then reacted with the suitably protected nucleotide containing an activated phosphite/phosphate. After each cycle the carrier bound nucleotide is preferably washed with anhydrous pyridine/acetonitrile (1:1, v/v), again deprotected, and the condensation reaction is completed in as many cycles as are required to form the desired number of congruent polarity internucleotide bonds which will be converted to phosphoramidates, phosphorodithioates, phosphorothioates or phosphodiesters as desired.

In one embodiment, to provide the switchback linker, the incoming activated, protected nucleoside is provided in the opposite polarity to the support-bound oligomers. Thus, for example, where the support-bound oligomer is 3'→5', the deprotected 5' hydroxyl is reacted with a 3'-protected, 5'-activated monomer, and the synthesis continued with monomers activated at the 5' position and protected at the 3' position.

In another embodiment, to provide the switchback linker, a dinucleoside synthon containing the linker element having one end which is activated for condensation (such as a hydrogen phosphonate) to the support-bound oligonucleotide and another end which is a protected hydroxyl group (or protected thio group) is condensed onto the support-bound oligonucleotide. The linked dinucleoside is condensed and deprotected using the same conditions as those used to condense and deprotect the protected nucleoside hydrogen phosphonate. Subsequent extension of the oligonucleotide chain then uses oligonucleotide residues which are activated and protected in the opposite manner from those used to synthesize the previous portion of the chain.

One approach to this synthesis, using a linker already derivatized to two nucleotide/nucleoside residues which will be included in each portion of the strand is illustrated in Reaction Scheme 2. The 5'→3' nucleotide portion of the strand is coupled using the 3' DMT-5'-activated phosphate nucleosides, as conventionally, to solid support. The switchback linker is derivatized to two nucleotide residues through their 3' positions; the remaining 5' positions are derivatized by the protecting group DMT in one nucleotide residue and a phosphonate residue in the other. The derivatized linker is coupled to the solid supported strand under standard reagent conditions and then deprotected conventionally. Further standard nucleotide coupling results in extension of the chain in the 3'→5' orientation.

A particularly preferred dimer synthon used to mediate the switchback in an oligomer is the O-xyloso linker (compounds 4 and 5 in Reaction Scheme 2). The O-xyloso linker consists of two xylose-nucleosides (1) linked to each other by o-xylene at the 3' position of each xylose sugar. The switchback linker synthon was synthesized using α,α'-dibromoxylene and 5'-DMT nucleoside (1) to give the dimer (2) as shown in Reaction Scheme 1 below. The dimer was converted to the H-phosphonate (A) and was used in solid phase synthesis to generate oligomers. Linkers containing the bases (at position "B" in Reaction Scheme 2) thymine, 5-methylcytosine, 8-hydroxy-$N^6$-methyladenine, pseudo-isocytosine or cytosine are synthesized as homodimers. However, the switchback linker dimers may also be synthesized as mixed heterodimers that are separated chromatographically.

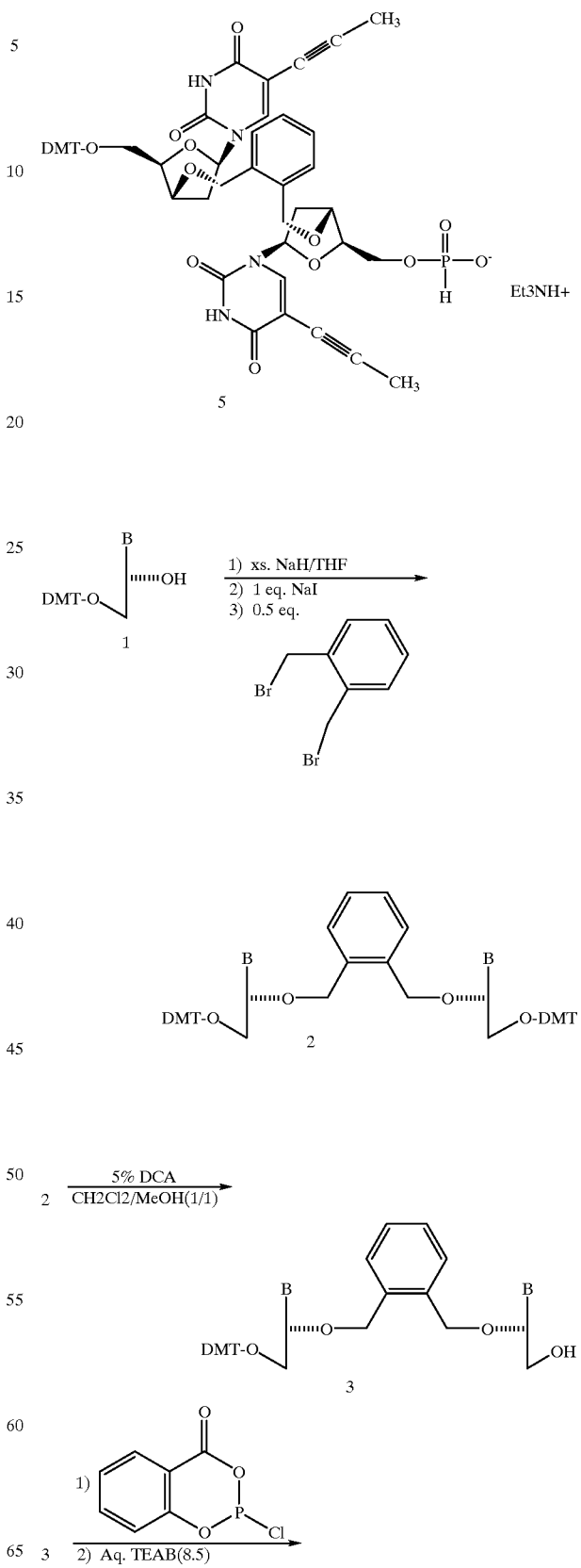

Reaction Scheme 2

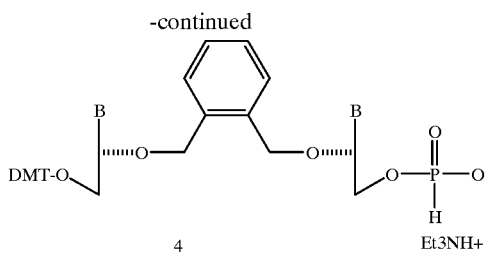

A particularly useful synthon in the preparation of oligomers containing inverted polarity is of the formula:

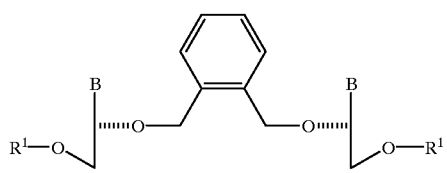

(6)

wherein each $R^1$ is H or a blocking group and each B is independently a purine or pyrimidine base, wherein one or both of these bases may optionally be the modified base residues of formula 1 and 2 of the invention.

2' Modified Oligomers

Included in some of the oligomers containing C-5 modified pyrimidines of the invention are modifications of the ribose or deoxyribose sugar. 2'-O-methyl-, 2'-O-ethyl- and 2'-O-allyloligo-ribonucleotides have been synthesized and shown to bind to single-stranded complementary nucleic acid sequences (Cotten, M., et al., *Nucleic Acids Res* (1990) 19:2629–2635; Blencowe, B. J., et al., *Cell* (1989) 59:531–539; Sproat, B. S., et al., *Nucleic Acids Res* (1989) 17:3373–3386; Inoue, H., et al., *Nucleic Acids Res* (1987) 15:6131–6148; Morisawa, H., et al., European Patent Publication No. 0339842; Chavis, C., et al., *J Organic Chem* (1982) 47:202–206; Sproat, B. S., et al, *Nucleic Acids Res* (1991) 19:733–738). The 2'-modified oligomers were reported to be relatively nuclease stable compared to unmodified controls. Synthesis of 2' fluoro nucleosides and their incorporation into oligonucleotides has also been described (Codington, J. F., et al, *J Org Chem* (1964) 29:558–564; Fazakerley, G. V., et al, *FEBS Lett* (1985) 182:365–369). Synthesis of oligonucleotide analogs containing the modified bases described herein would be based on methods described.

Synthesis of 2'-thioalkyl nucleosides is accomplished as described in Reaction Scheme 3. The protocol is useful for synthesis of 2'-thioalkyl pyrimidines which permit formation of an anhydro intermediate (2) that is subsequently converted to thioalkyl nucleoside (3). The protocol was used to synthesize 5' DMT blocked 5-methyluridine 3' H-phosphonate. The starting material (1) was obtained from 5-methyluridine (Markiewicz, W. T., *J. Chem. Res (M)* (1979) 0181–0197. Alternate blocking groups at the 5' and 3' positions, such as tetrahydropyran may also be utilized to obtain an equivalent starting material. Scheme II may thus be used to synthesize 2'-thioalkyl derivatives of the nucleosides containing the modified bases of the present invention in addition to synthesis of other modified pyrimidine nucleosides such as 2'-thioalkylcytidine, 2'-thioalkylthymidine, 2'-thioalkyl-$N^4$-N-ethanocytidine or 2'-thioalkyluridine. Conversion of the nucleoside (3) to other 5' and 3' derivatized compounds such as MMT, β-cyanoethylphosphoramidite, or methylphosphoramidite-blocked nucleosides can easily be accomplished using appropriate reagents. (The group designated W may be lower alkane (methyl, ethyl, propyl, isopropyl, butyl or isobutyl) or lower alkene (allyl).)

Reaction Scheme 3

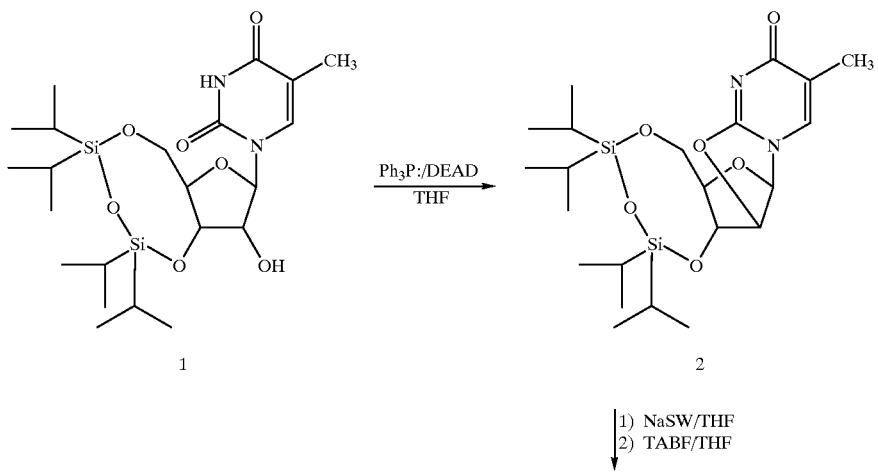

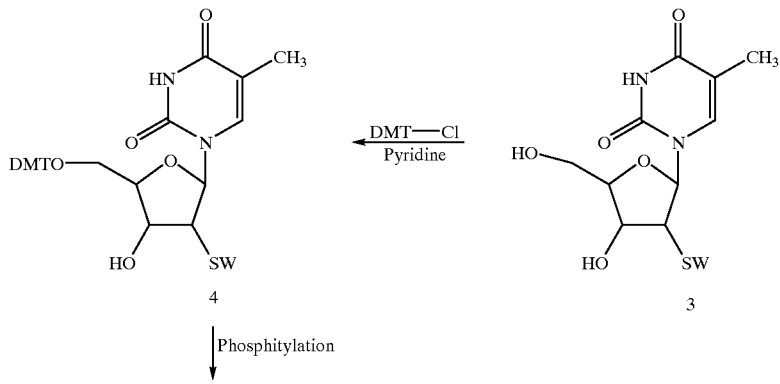

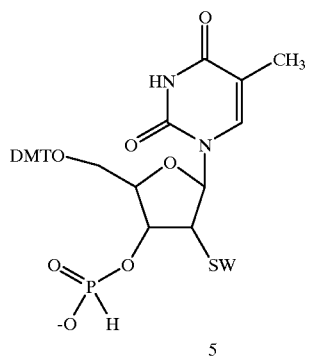

Dimer Synthons for Oligomers Containing Substitute Linkages

Oligomers containing substitute linkages that link adjacent nucleotide analog residues are preferably synthesized using suitably blocked dimer synthons as a starting material. For dimers wherein one or both base residues are 5-$R^2$-U or 5-$R^2$-C or related analogs, synthesis of a formacetal or 3'-thioformacetal-linked dimer is accomplished as described above. One or both starting monomers would consist of nucleosides containing 5-$R^2$-U or 5-$R^2$-C instead of conventional nucleosides. An exemplary dimer containing a formacetal linkage is of the formula:

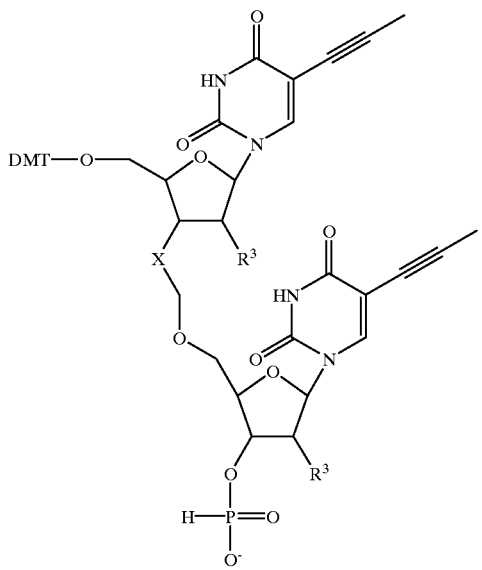

$R^3$ is as defined above and, in preferred embodiments, X is either O or S. Dimer synthons that are included in the scope of the present invention contain 5-$R^2$-U, 5-$R^2$-C or as one or both of the bases and may include (i) other substitute linkages such as the 3' amine linkage, (ii) other purines, pyrimidines or their analogs as described above or (iii) other 3' and 5' groups such as H, MMT, or an amidite as described above. Dimer synthons are incorporated into oligomers using any standard technique.

"Blocking Groups"

As used herein, "blocking group" refers to a substituent other than H that is conventionally coupled to oligomers or nucleosides, either as a protecting group, an activated group for synthesis, $PO_3^{-2}$, or other conventional conjugate partner such as a solid support, label, immunological carrier and the like. Suitable protecting groups are, for example, DMT or MMT; suitable activated groups are, for example, H-phosphonate, methyl phosphonamidite, methylphosphoramidite or β-cyanoethylphosphoramidite. In general, the nucleosides and oligomers of the invention may be derivatized to such "blocking groups" as indicated in the relevant formulas.

Utility and Administration

As the oligonucleotides of the invention are capable of significant single-stranded or double-stranded target nucleic acid binding activity to form duplexes, triplexes or other forms of stable association, these oligonucleotides are useful in diagnosis of diseases that are associated with expression of one or more genes such as those associated with viral infections due to say, HIV, HCMV, HSV or HPV. Exemplary genes that may be targeted would encode adhesion molecules, receptor molecules or oncogenes that may be associated with inflammatory conditions, immune reactions or cancer respectively. Diagnostic applications for the oligomers described herein includes their use as probes for detection of specific sequences by any standard method.

In addition, the oligomers of the invention may be used as diagnostic reagents to detect the presence or absence of the target gene sequences to which they specifically bind. Such diagnostic tests are conducted by hybridization through either double or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

The use of oligomers containing the modified bases as diagnostic agents by triple helix formation is advantageous since triple helices form under mild conditions and the assays may thus be carried out without subjecting test specimens to harsh conditions. Diagnostic assays based on detection of RNA for identification of bacteria, fungi or protozoa sequences often require isolation of RNA from samples or organisms grown in the laboratory, which is laborious and time consuming; as RNA is extremely sensitive to ubiquitous nucleases.

The oligomer probes may also incorporate additional modifications such as altered internucleotide linkages that render the oligomer especially nuclease stable, and would thus be useful for assays conducted in the presence of cell or tissue extracts which normally contain nuclease activity. oligonucleotides containing terminal modifications often retain their capacity to bind to complementary sequences without loss of specificity (Uhlmann et al., *Chemical Reviews* (1990) 90:543–584). As set forth above, the invention probes may also contain linkers that permit specific binding to alternate DNA strands by incorporating a linker that permits such binding (Horne et al., *J Am Chem Soc* (1990) 112:2435–2437).

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

The following examples are intended to illustrate, but not to limit, the invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLE 1

Synthesis of 5-Propynyl 2'-deoxyuridine H-Phosphonate Monomer and Oligomers Containing the Analog In a 50 mL round bottom flask is placed:
a) 708 mg (2 mmole) 5-iodo dU
b) 10 mL anhydrous DMF
c) 76 mg (0.4 mmole) CuI
d) 555 μL (4 mmole) $Et_3N$
e) 231 mg (0.2 mmole) $(Ph_3P)_4Pd$
f) saturate with propyne gas with stirring at room temperature (approx. 10 min.).

After 2 hours, more propyne gas is bubbled in and the reaction mixture is stirred overnight at room temperature. The following morning more propyne is bubbled in and stirred for an additional 2 hrs. To the reaction mixture is added Dowex ion-exchange resin ($HCO_3$-form), 10 mL of MeOH and 10 mL of $CH_2Cl_2$ and stirring continued for 1 hr. The resin is filtered off, washed with MeOH and the supernatant evaporated. Silica Gel chromatography yielded 517 mg (1.94 mmole, 97% yield) of product. See: Hobbs, *J Org Chem* (1989) 54:3420–3422.

The purified material was protected with a 5' DMT and phosphytylated as described (Marugg, J. E., et al, *Tetrahedron Letters* (1986) 27:2661–2664) and used in solid phase synthesis as described (Froehler, B. C., et al, U.S. Pat. No. 4,959,463; Froehler, B. C., et al, *Tetrahedron Letters* (1986) 27:5575–5578).

The following notation is used to represent the bases in the designated numbered oligomers in the Examples below: A, T, G, C, and U have their conventional meanings. C'=5 methyl cytosine, C*=5-propynyl cytosine; U*=5-propynyl uracil.

EXAMPLE 2

Formation of Triple Helix Structures Using Oligomers Containing 5-Propynyl Uracil Residues that Bind to Duplex DNA Three oligomers were synthesized as follows:
ODN-1 5'TC'TC'TC'TC'TC'TTTTT 3' (SEQ ID NO: 2)

ODN-2 5'TC'TC'TC'TC'TC'U*U*U*U*U* 3' (SEQ ID NO: 3)

ODN-3 5'TC'TC'TC'U*C'U*C'U*TU*TU* 3' (SEQ ID NO: 4)

The oligomer was hybridized with duplex DNA containing the target sequence 5'AGAGAGAGAGAAAAA 3' (SEQ ID NO: 5). Hybridization was carried out in 140 mM KCl, 5 MM MgCl$_2$, 5 mM Na$_2$HPO$_4$, pH 6.6. Thermal stability, T$_m$, of the resulting triple helix formed between each oligomer and the target sequence was determined. The following T$_m$ values were obtained, ODN-1 (control oligomer) was 42.1° C., ODN-2 was 48.1° C. and ODN-3 was 55° C. The increased T$_m$ values of ODN-2 and ODN-3 were not expected and demonstrated that the triple helix formed was more stable than the corresponding control triple helix structure.

EXAMPLE 3

Binding of Oligomers Containing 5-Propynyl Uracil or 5-Propynyl Cytosine to Single-Stranded RNA Oligomers were synthesized as follows:

ODN-1 5' TC'TC'TC'TC'TC'TTTTT 3' (SEQ ID NO: 2)

ODN-3 5' TC'TC'TC'U*C'U*C'U*TU*TU* 3' (SEQ ID NO: 3)

ODN-4 5' TC*TC*TC*TC*TC*TTTTT 3, (SEQ ID NO: 6)

The oligomers were hybridized with a single-stranded target RNA sequence, 5' AAAAAGAGAGAGAGA 3', in (SEQ ID NO: 7) 140 mM KCl, 5 mM MgCl$_2$, 5 mM Na$_2$HPO$_4$, pH 6.6. The following T$_m$ values for the duplexes were obtained; ODN-1 (control) was 65.5° C., ODN-3 was 74.0° C. and ODN-4 was 73.0° C. Duplexes formed with ODN-3 and ODN-4 were more stable than the control oligomer.

EXAMPLE 4

Formation of Triple Helix Structures at Elevated pH

Triple helix formation at elevated pH was demonstrated using ODN-1 as a control and ODN-5, 5'U*C'U*C'U*C'U*C'U*U*U*U*U* 3' (SEQ ID NO: 8). Oligomers were hybridized with duplex target DNA, as described in Example 2 except that the buffer was at pH 7.4. T$_m$ values of the triple helix were then determined. ODN-1 had a T$_m$ of 27.1 while ODN-5 had a T$_m$ of 51.5. Thus, oligomers containing 5-propynyl uracil were capable of triplex formation at high pH levels, while the control oligomer formed triplex structure only at temperatures that are below physiological.

In an additional set of determinations, modified forms of ODN-5 wherein the 5-substituent was, instead of propynyl, 3-methylbutynyl (ODN-5A) or 3,3-dimethyl butynyl (ODN-5B), similar affects on the melting temperature of duplex and triple helices were observed. The results are shown in Table 1 below:

TABLE 1

| | Duplex [a] | | Triple-helix [a] | |
|---|---|---|---|---|
| | RNA | DNA | @ pH = 6.60 | |
| | T$_m$ (° C.) | T$_m$ (° C.) | T$_m$ (° C.) | ΔT$_m$ (° C.) |
| ODN-1 | 63.0 | 54.5 | 39.6 | — |
| ODN-5 | 79.0 | 65.5 | 64.8 | +25.2 |
| ODN-5A | 73.5 | 65.5 | 55.9 | +16.3 |
| ODN-5B | 68.5 | 66.0 | 42.5 | +2.9 |

[a] T$_m$ in 140 mM KCl/5 mM Na$_2$PO$_4$/1 mM MgCl$_2$, pH 6.60.

EXAMPLE 5

Synthesis of 3-Methyl-1-Butynyldeoxyuridine (bdU) H-Phosphonate. Oligomers Containing the Analog and Formation of Triple Helix Structures Using the Oligomers bdU was synthesized from 5-iododeoxyuridine essentially as described for pdU in Example 1, except that 5 equivalents of 3-methyl-1-butyne liquid was used in place of propyne. Silica gel purified material was then converted to the 5'DMT, 3' H-phosphonate monomer and used in solid phase synthesis to generate oligomers as follows (ODN-1 was used as a control containing thymine and 5-methylcytosine as described in Example 2):

ODN-1 5' TC'TC'TC'TC'TC'TTTTT 3' (SEQ ID NO: 2)

ODN-6 5' TC'TC'TC'U'C'U'CU'TU'TU'3' (SEQ ID NO: 4)

ODN-7 5' TC'TC'TC'TC'TC'U'U'U'U'U'3 (SEQ ID NO: 10)

Base residues designated U' correspond to bdU. The oligomers were hybridized with duplex DNA containing the target sequence, 5' AGAGAGAGAGAAAAA 3' (SEQ ID NO: 5). Hybridization was carried out in the buffer described in Example 2 at pH 6.2. ODN-1 had a T$_m$ of 51.0° C. while the T$_m$ of ODN-6 was 55.2° C. and that of ODN-7 was 55.0° C.

Synthesis of 5-phenyldeoxyuridine was accomplished as previously described using phenyltrimethylstannane (Crisp, G., et al., *Tetrahedron Letters* (1990) 31:1347–1350). A similar protocol using pyridinyltrimethylstannane as a starting material which is obtained from bromopyridine would be used to synthesize 5-pyridinyluridine.

Synthesis of pyrimidine nucleosides with 2-thiazoyl, 1-methyl-2-imidazoyl, 2-imidazoyl and 2-isoxazoyl modification of the 5-position can be accomplished using a published protocol (Wigerinck, P. et al., *J Med Chem* (1991) 34:2383–2389) followed by conversion to the corresponding nucleotide by standard methods.

EXAMPLE 6

Additional oligomers were tested with respect to melting point after complexation with DNA or RNA targets. The targets were as follows:

DNA Duplex Target: 5' AGAGAGAGAGAAAAAGGA$^T$T (SEQ ID NO: 11) 3' TCTCTCTCTCTTTTTCCT$_T$ T (SEQ ID NO: 12)

RNA Target: 5' AAAAAGAGAGAGAGA 3' (SEQ ID NO: 13)

The assays for triple-helix binding were conducted in 140 mM KCL/5 mM Na$_2$HPO$_4$/5 mM MgCL$_2$ at pH=6.60 and the final concentration of all oligodeoxynucleotides was ~2 μM.

ODN-1, set forth above, was used as a control.

Test oligomers 8–10 contain substitutions of 5-propynyluracil for thymine and 5-propynylcytosine for methylcytosine.

ODN-8 5'-TC'TC'TC'U*C'U*C'U*TU*TU* 3' (SEQ ID NO: 4)

ODN-9 5-TC*TC*TC*TC*TC*TTTTT 3' (SEQ ID NO: 2)

ODN-10 5'-U*C*U*C*UC*U*C*U*U*C*U*U*U*U 3, (SEQ ID NO: 14)

The results obtained showed that, with respect to triple-helix formation, the control ODN-1 gave a $T_m$ of 43.4° C.; ODN-8 gave an elevated $T_m$ of 55.5° C.; and ODN-9 gave a $T_m$ of 26.3° C.; ODN-10 was not tested. ODN-8 containing U*, showed an increase in $T_m$ of 2.4° C./substitution ($\Delta T_m$@6.6=+12.1° C.) relative to ODN-1 and ODN-9, containing C*, showed a decrease in $T_m$ of 3.4° C./substitution ($\Delta T_m$@6.6=−17.1° C.) relative to ODN-1. The $T_m$ of a triple-helix, in which the third strand contains 2'-deoxycytidines, is pH dependent, and the $T_m$ at different pH values (from 5.8 to 7.4) was used to examine the pH dependence of the complex. With all ODN's the slope of the plot remained relatively constant (−18 to −20° C./pH unit).

ing a heterocycle modification that enhances binding affinity (defined herein as a positive modification), such as U* or C*, and a modification that reduces affinity (defined herein as a negative modification), were found to have improved binding (i.e. a greater binding affinity than predicted by the additive effects—positive and negative—of both modifications), relative to oligomers containing only the negative modification. surprisingly, the propyne modification potentiates the negative binding effect of the phosphorothioate linkages to an unexpected degree. That is, for oligomers containing T and C' the $\Delta T_m$ between diester and thioate is 14° C. (0.7° C. per substitution) while the $\Delta T_m$ with U* and C* is 6.0° C. (0.3° C. per substitution). These results clearly demonstrate a synergistic effect between the negative modification (thioate linkage) and the positive modification (5-substituted pyrimidine) wherein the positive modification compensated to a degree that is more than additive with respect to binding affinity. Binding results ($\Delta T_m$ relative to diester linkages) that were obtained are shown in Table 2 below:

TABLE 2

| ODN | | Diester | Thioate ($\Delta T_m$) |
|---|---|---|---|
| ATTTTC'TTC'ATTTTTTC'TTC' | (SEQ ID NO:15) | 54.0 | 40.0—14.0 |
| AU*U*U*U*C'U*U*C'AU*U*U*U*U*C'U*U*C' | (SEQ ID NO:16) | 76.5 | 68.5—8.0 |
| AU*U*U*U*C*U*U*C*AU*U*U*U*U*C*U*U*C* | (SEQ ID NO:17) | 82.5 | 76.5—6.0 |

The low $T_m$ of ODN-8, relative to ODN's 1 and 7, can be explained in terms of basicity of the heterocycle. Titration of the hydrocholoride salt of C* and C' showed that the pKa of the 5-propyne analog C* (3.30,±0.05) is 1.05 units less than the 5-methyl derivative C' (4.35,±0.05). The importance of protonation in triple-helix formation has been demonstrated and the results above indicate that a decrease in basicity of the cytosine nucleobase has a dramatic effect on the stability of the complex. Surprisingly, the large difference in pKa's of the cytosines (C* and C') has no significant effect on the slope of the $T_m$ vs pH plot.

With respect to DNA/RNA duplex formation, the control, ODN-1 had a $T_m$ of 65.5° C., ODN-8 had a $T_m$ of 74.0° C., ODN-9 had a $T_m$ of 73.0° C. and ODN-10 had a $T_m$ of more than 90° C.; ODN-8 containing U*, results in an increase in $T_m$ of 1.7° C./substitution and ODN-9, containing C*, results in an increase in $T_m$ of 1.5° C./substitution. Under these conditions ODN-10, containing complete substitution with U* and C*, has a $T_m$ greater than 90° C. (approx. 1.7° C./substitution) indicating that the increase in binding affinity of these substitutions are additive. These results show that the double-helix complex is greatly stabilized by substitution with both C* and U* and, therefore, these analogs represent a new class of useful antisense ODN's.

Binding assays were conducted using a combination of C* and U* in oligomers containing thioate internucleotide linkages as an additional modification. Thioate linkages render oligomers nuclease stable, but reduce binding affinity for complementary target sequences relative to unmodified phosphodiester linkages. Other phosphodiester linkage analogs known in the art such as alkylphosphonate, methylphosphonate, amidate and triester linkages suffer from similar limitations. Unexpectedly, oligomers contain- Additional oligonucleotides designed to target T antigen in a modification of the in vivo antisense assay described by Graessmann, M. et al. *Nucleic Acids Res* (1991) 19:53–59 were also modified to contain U* and/or C* as well as modified internucleoside linkages. The Graessmann assay uses an expression vector for SV40 T antigen and oligonucleotides designed to target a purine-rich region in the coding sequence were employed. Thus, the oligonucleotides used in this assay were as follows:

ODN 11:5'-ATTTTC'TTC'ATTTTTTC'TTC' 3' (SEQ ID NO: 15)

ODN 12: thioated form of ODN-11

ODN 13:5'-AU*U*U*C*U*U*C*AU*U*U*U*C*U*C*U*U*C* 3' (SEQ ID NO: 18)

ODN 14: thioated form of ODN-13

ODN 15: thioated 5° C*U*U*C*AU*U*U*U*U* 3' (SEQ ID NO: 19)

ODN 16: thioated 5° C*U*U*C*AU*U*U* 3' (SEQ ID NO: 20)

The melting points of the tested oligomers with the complementary RNA were also determined as described above as well as the halflife of the oligomer in the cells and the ability of the oligomer to inhibit T antigen synthesis. The ability of compound to confer RNAseH sensitivity on the bound RNA was also determined. The results are shown in Table 3.

TABLE 3

| Oligomer | RNA T*$_m$ | T$_{1/2}$ | TAg Inh. | RNAseH |
|---|---|---|---|---|
| ODN-11 | 54.0° | – | – | + |
| ODN-12 | 40.0° | +++ | – | + |
| ODN-13 | 82.5° | – | +/– | N.D. |
| ODN-14 | 76.5° | +++ | +++ | N.D. |
| ODN-15 | 53.5° C. | +++ | + | N.D. |
| ODN-16 | 48.0° C. | +++ | – | N.D. |

*T$_m$ determined under the same conditions as previously described at pH 6.6.

As seen, substituting the thioate linkage for diester decreases the affinity for target RNA but enhances the halflife of the oligomers in the cell. Replacement of the thymine and cytosine bases by the 5-substituted bases of the invention enhanced affinity but fails to increase halflife, but at an increased concentration of oligomer, the enhanced affinity of the oligomer led to slight T antigen synthesis inhibition (ODN-13). On the other hand, the thioate analog containing the modified bases is sufficiently stable and has sufficient affinity for the RNA to effect inhibition of the synthesis of T antigen.

An 11-mer thioate was also able to inhibit T antigen synthesis when it contained the 5-substituted bases of the invention.

Further experiments using this assay system using a different T antigen target sequence demonstrated that substitution of the modified oligomers of the invention containing diester linkages but containing 2'-O-allyl substitutions in the oligomers containing fully substituted nucleosides wherein C* replaces C and U* replaces T are capable of inhibiting T antigen synthesis.

Additional data obtained in vitro with respect to duplex formation with target RNA corresponding to T antigen show that the binding of the oligomer to the target is sequence-specific for the 5-substituted oligomers of the invention. The additional oligomers, 17 and 18, were prepared; ODN-18 is a scrambled form of ODN-17 which is designed to target the T antigen purine-rich region as described above.

ODN-17:
AU*U*U*U*C'U*U*C'AU*U*U*U*U*C'U*U*C' (SEQ ID NO: 16) ODN-18: U*U* A U*U* A U*C'U*U*C'U*U*C'U*U*U*U*C'U* (SEQ ID NO: 21)

The oligomers were tested in diester and thioated form; ODN-17A and ODN 18A the thioates; ODN-17B and ODN-18B the 2'-O-allyl T and C' oligomers. The results are shown in Table 4 below:

TABLE 4

| ODN-17 | 76.5 |
|---|---|
| ODN-18 | 53.0 |
| ODN-17A | 68.0 |
| ODN-18A | 42.0 |
| ODN-17B | 70.0 |
| ODN-18B | 45.0 |

The differences in T$_m$ between the scrambled and unscrambled form are roughly the same regardless of the pyrimidine or backbone substitution used.

The instant invention is shown and described herein in what is considered to be the most practical and preferred embodiments. It is recognized, however, that departures may be made therefrom which are within the scope of the invention, and that modifications will occur to those skilled in the art upon reading this disclosure.

What is claimed is:

1. A method making an oligonucleotide, comprising the steps:
   (a) selecting a first oligonucleotide comprising a first covalent modification and a second covalent modification, said first covalent modification selected from the group consisting of a modified sugar, a modified base and a modified linkage and said second covalent modification selected from the group consisting of a modified sugar, a modified base and a modified linkage, wherein said first covalent modification increases the binding affinity of said first oligonucleotide for a complementary nucleic acid sequence relative to an otherwise identical unmodified second oligonucleotide that does not comprise said first covalent modification or said second covalent modification, and wherein said second covalent modification decreases the binding affinity of said first oligonucleotide for the complementary nucleic acid sequence relative to said otherwise identical unmodified second oligonucleotide that does not comprise the first covalent modification or the second covalent modification and wherein said second covalent modification results in a property selected from the group consisting of increased nuclease stability and enhanced cellular permeation in said first oligonucleotide for a complementary nucleic acid sequence relative to said otherwise identical unmodified second oligonucleotide;

(b) measuring the affinity of said first oligonucleotide for a complementary nucleic acid sequence;

(c) selecting an oligonucleotide of step (b) having a binding affinity for the complementary nucleic acid sequence that is greater than the sum of the increased binding affinity and the decreased binding affinity; and (d) preparing the oligonucleotide of step (c).

2. The method of claim 1 wherein the first covalent modification is a modified purine or pyrimidine.

3. The method of claim 1 wherein the modified purine or pyrimidine is a 5-substituted pyrimidine.

4. The method of claim 1 wherein the second covalent modification is a modified internucleotide linkage.

5. The method of claim 1 wherein he modified internucleotide linkage is selected from the group consisting of thioate, dithioate, 1–12C alkylphosphonate, amidate and triester.

6. The method of claim 1 wherein the complementary nucleic acid is duplex DNA, single-stranded RNA or single-stranded DNA.

7. The method of claim 5 wherein the 1–12C alkylphosphonate linkage is a methylphosphonate linkage.

* * * * *